United States Patent
Strauss et al.

(10) Patent No.: US 9,295,494 B2
(45) Date of Patent: Mar. 29, 2016

(54) SPINE STABILIZATION SYSTEM

(75) Inventors: Kevin R. Strauss, Leesburg, VA (US); Scott Jones, McMurray, PA (US); Jennifer Moore, Summit Point, WV (US); Michael Barrus, Ashburn, VA (US); Oheneba Boachie-Adjei, Briarcliff, NY (US); Robert Clinton Boyd, Winchester, VA (US)

(73) Assignee: K2M, Inc., Leesburg, VA (US)

( * ) Notice: Subject to any disclaimer, the term of this patent is extended or adjusted under 35 U.S.C. 154(b) by 243 days.

(21) Appl. No.: 13/636,416

(22) PCT Filed: Jun. 28, 2011

(86) PCT No.: PCT/US2011/042127
§ 371 (c)(1),
(2), (4) Date: Nov. 8, 2012

(87) PCT Pub. No.: WO2012/006064
PCT Pub. Date: Jan. 12, 2012

(65) Prior Publication Data
US 2013/0144342 A1    Jun. 6, 2013

Related U.S. Application Data

(60) Provisional application No. 61/359,028, filed on Jun. 28, 2010.

(51) Int. Cl.
*A61B 17/70* (2006.01)
*F16D 1/00* (2006.01)
*A61B 17/88* (2006.01)

(52) U.S. Cl.
CPC .............. *A61B 17/701* (2013.01); *A61B 17/70* (2013.01); *A61B 17/7002* (2013.01); *A61B 17/8863* (2013.01); *A61B 17/7035* (2013.01)

(58) Field of Classification Search
CPC .......................... A61B 17/7004; A61B 17/701
USPC .................................. 606/261–262, 264–270
See application file for complete search history.

(56) References Cited

U.S. PATENT DOCUMENTS 4,653,481 A * 3/1987 Howland et al. .............. 606/261
5,261,912 A    11/1993 Frigg
(Continued)

FOREIGN PATENT DOCUMENTS

JP    2009-535113 A    10/2009

OTHER PUBLICATIONS

International Search Report mailed Oct. 28, 2011 from corresponding International Application No. PCT/US2011/042127, filed Jun. 28, 2011 (1 pg.).

(Continued)

*Primary Examiner* — Ellen C Hammond
*Assistant Examiner* — Stuart S Bray
(74) *Attorney, Agent, or Firm* — Carter, DeLuca, Farrell & Schmidt, LLP

(57) ABSTRACT

A spinal stabilization system includes a connecting rod, a rod bending device, and a plurality of bone screws. The connecting rod includes an elongate round portion, an elongate head portion and a neck portion connecting the elongate round portion with the elongate head portion. The rod bending device includes an elongate body defining an aperture configured and dimensioned to receive the connecting rod therethrough in a single orientation. The bone screws include a housing portion and a screw shaft distally extending from the housing portion. The housing portion includes an inner housing and an outer housing slidably surrounding at least a portion of the inner housing. The inner housing defines a slot configured and dimensioned to releasably secure the elongate round portion of the connecting rod therein. The outer housing is movable relative to the inner housing between an unlocked state and a locked state.

32 Claims, 33 Drawing Sheets

(56) References Cited

U.S. PATENT DOCUMENTS

| | | | |
|---|---|---|---|
| 5,282,863 A * | 2/1994 | Burton | 606/254 |
| 5,382,248 A * | 1/1995 | Jacobson et al. | 606/60 |
| 5,389,099 A | 2/1995 | Hartmeister et al. | |
| 5,437,669 A * | 8/1995 | Yuan et al. | 606/278 |
| 5,562,660 A * | 10/1996 | Grob | 606/258 |
| 5,591,235 A * | 1/1997 | Kuslich | 606/261 |
| 5,593,408 A * | 1/1997 | Gayet et al. | 606/261 |
| 5,658,286 A | 8/1997 | Sava | |
| 5,667,508 A | 9/1997 | Errico et al. | |
| 5,899,904 A | 5/1999 | Errico et al. | |
| 5,947,969 A | 9/1999 | Errico et al. | |
| 6,102,912 A * | 8/2000 | Cazin et al. | 606/86 A |
| RE37,479 E * | 12/2001 | Kuslich | 623/17.11 |
| 6,440,133 B1 | 8/2002 | Beale et al. | |
| 6,451,021 B1 | 9/2002 | Ralph et al. | |
| 6,482,207 B1 | 11/2002 | Errico | |
| 6,540,749 B2 * | 4/2003 | Schafer et al. | 606/270 |
| 6,582,434 B2 | 6/2003 | Kawakami et al. | |
| 6,644,087 B1 | 11/2003 | Ralph et al. | |
| 6,648,886 B2 * | 11/2003 | Nohara et al. | 606/261 |
| 6,966,910 B2 * | 11/2005 | Ritland | 606/257 |
| 7,488,331 B2 | 2/2009 | Abdelgany | |
| 7,503,918 B2 | 3/2009 | Baccelli et al. | |
| 7,507,248 B2 * | 3/2009 | Beaurain et al. | 606/261 |
| 7,520,879 B2 | 4/2009 | Justis et al. | |
| 7,563,274 B2 * | 7/2009 | Justis et al. | 606/279 |
| 7,569,061 B2 | 8/2009 | Colleran | |
| 7,588,575 B2 | 9/2009 | Colleran et al. | |
| 7,588,588 B2 | 9/2009 | Spitler et al. | |
| 7,604,653 B2 | 10/2009 | Kitchen | |
| 7,618,442 B2 | 11/2009 | Spitler et al. | |
| 7,658,739 B2 * | 2/2010 | Shluzas | 606/250 |
| 7,766,942 B2 * | 8/2010 | Patterson et al. | 606/261 |
| 7,931,676 B2 * | 4/2011 | Veldman et al. | 606/261 |
| 7,947,064 B2 * | 5/2011 | Bergeron et al. | 606/263 |
| 7,988,694 B2 * | 8/2011 | Barrus et al. | 606/86 A |
| 8,016,828 B2 * | 9/2011 | Shluzas | 606/250 |
| 8,546,456 B2 * | 10/2013 | Rose et al. | 521/88 |
| 8,641,735 B2 * | 2/2014 | Serbousek | 606/259 |
| 8,894,657 B2 * | 11/2014 | Jackson | 606/86 A |
| 9,011,501 B2 * | 4/2015 | Mikhail et al. | 606/305 |
| 9,050,139 B2 * | 6/2015 | Jackson | |
| 9,101,426 B2 * | 8/2015 | Forderer et al. | |
| 2002/0161368 A1 | 10/2002 | Foley et al. | |
| 2003/0144666 A1 * | 7/2003 | Bagga et al. | 606/61 |
| 2003/0191470 A1 * | 10/2003 | Ritland | 606/61 |
| 2003/0225408 A1 | 12/2003 | Nichols et al. | |
| 2004/0172020 A1 * | 9/2004 | Beaurain et al. | 606/61 |
| 2004/0215191 A1 * | 10/2004 | Kitchen | 606/61 |
| 2004/0254577 A1 * | 12/2004 | Delecrin et al. | 606/61 |
| 2005/0065515 A1 | 3/2005 | Jahng | |
| 2005/0273099 A1 * | 12/2005 | Baccelli et al. | 606/61 |
| 2006/0009768 A1 * | 1/2006 | Ritland | 606/61 |
| 2006/0189982 A1 * | 8/2006 | Lange | 606/61 |
| 2007/0042633 A1 * | 2/2007 | Frigg et al. | 439/377 |
| 2007/0093817 A1 * | 4/2007 | Barrus et al. | 606/61 |
| 2007/0186990 A1 * | 8/2007 | Serbousek | 138/135 |
| 2007/0191841 A1 | 8/2007 | Justis et al. | |
| 2008/0027432 A1 * | 1/2008 | Strauss et al. | 606/61 |
| 2008/0086130 A1 * | 4/2008 | Lake et al. | 606/61 |
| 2008/0091214 A1 * | 4/2008 | Richelsoph | 606/103 |
| 2008/0177320 A1 * | 7/2008 | McBride | 606/261 |
| 2009/0018593 A1 | 1/2009 | Barrus et al. | |
| 2009/0105716 A1 * | 4/2009 | Barrus | 606/103 |
| 2009/0105769 A1 * | 4/2009 | Rock et al. | 606/308 |
| 2009/0292308 A1 * | 11/2009 | Jones et al. | 606/205 |
| 2010/0063544 A1 * | 3/2010 | Butler | 606/261 |
| 2010/0114170 A1 * | 5/2010 | Barrus et al. | 606/264 |
| 2010/0222818 A1 * | 9/2010 | Trieu et al. | 606/254 |
| 2010/0301098 A1 * | 12/2010 | Kostrzewski | 227/179.1 |
| 2011/0029018 A1 * | 2/2011 | Carlos | 606/246 |
| 2011/0152936 A1 * | 6/2011 | Gil et al. | 606/259 |
| 2011/0172714 A1 * | 7/2011 | Boachie-Adjei et al. | 606/264 |
| 2011/0190823 A1 * | 8/2011 | Bergeron et al. | 606/264 |
| 2012/0083853 A1 * | 4/2012 | Boachie-Adjei et al. | 606/86 A |
| 2012/0136394 A1 * | 5/2012 | Calvosa et al. | 606/254 |
| 2013/0066375 A1 * | 3/2013 | Biedermann et al. | 606/260 |
| 2013/0072980 A1 * | 3/2013 | Biedermann et al. | 606/254 |
| 2013/0158606 A1 * | 6/2013 | Freudiger et al. | 606/264 |
| 2014/0114360 A1 * | 4/2014 | Gephart et al. | 606/279 |
| 2014/0135843 A1 * | 5/2014 | Barrus | 606/270 |
| 2014/0135844 A1 * | 5/2014 | Ark et al. | 606/270 |
| 2014/0148855 A1 * | 5/2014 | Beaurain et al. | 606/264 |
| 2014/0257393 A1 * | 9/2014 | Trieu et al. | 606/254 |

OTHER PUBLICATIONS

Japanese Office Action dated Oct. 6, 2015 in corresponding JP Application No. 2013-518562.

* cited by examiner

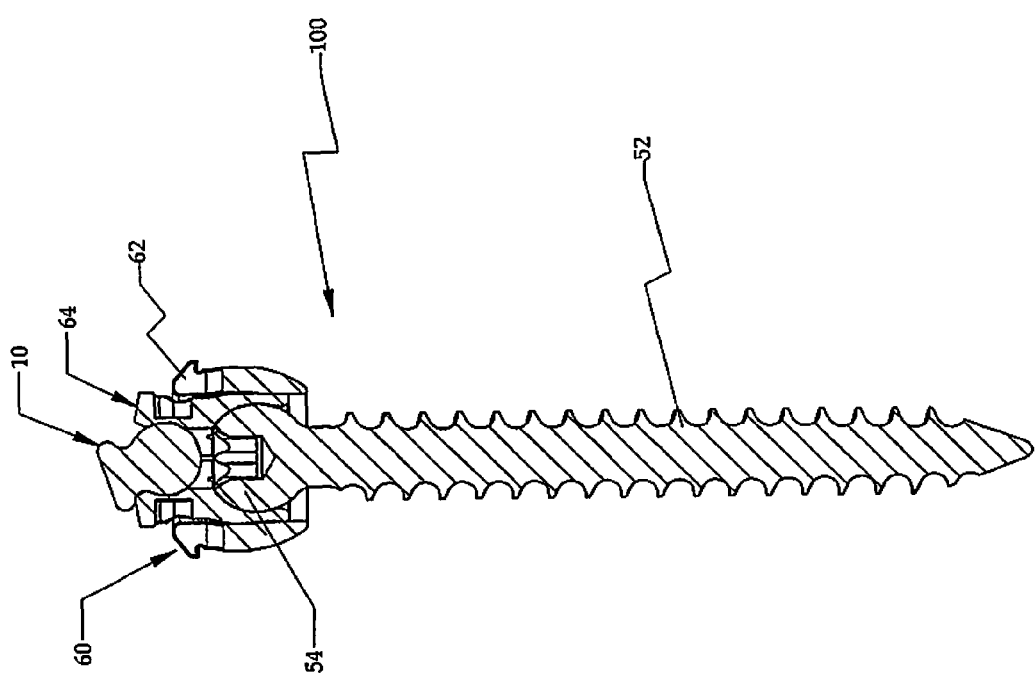

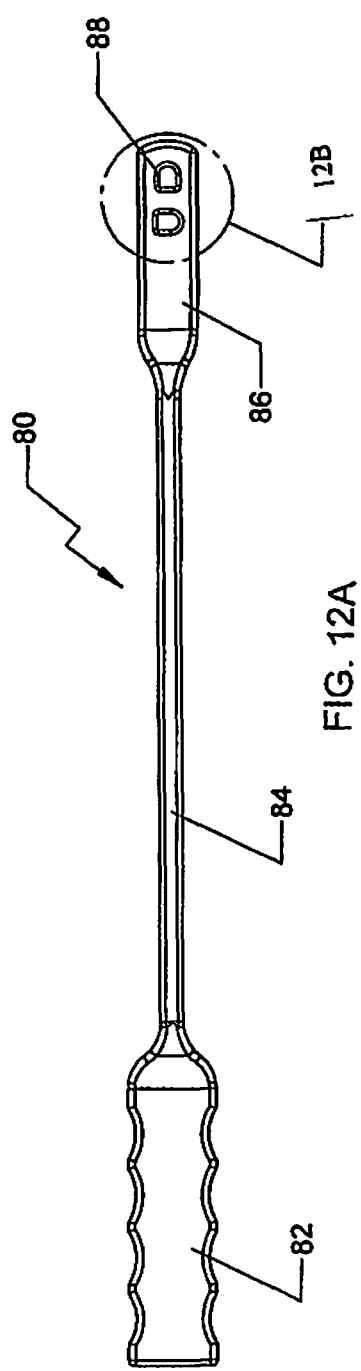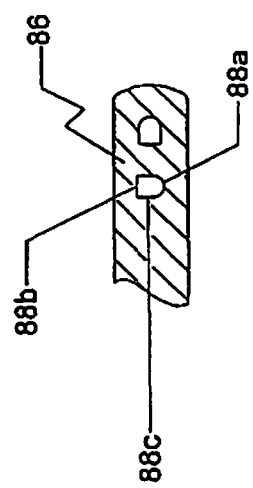
FIG. 12A
FIG. 12B

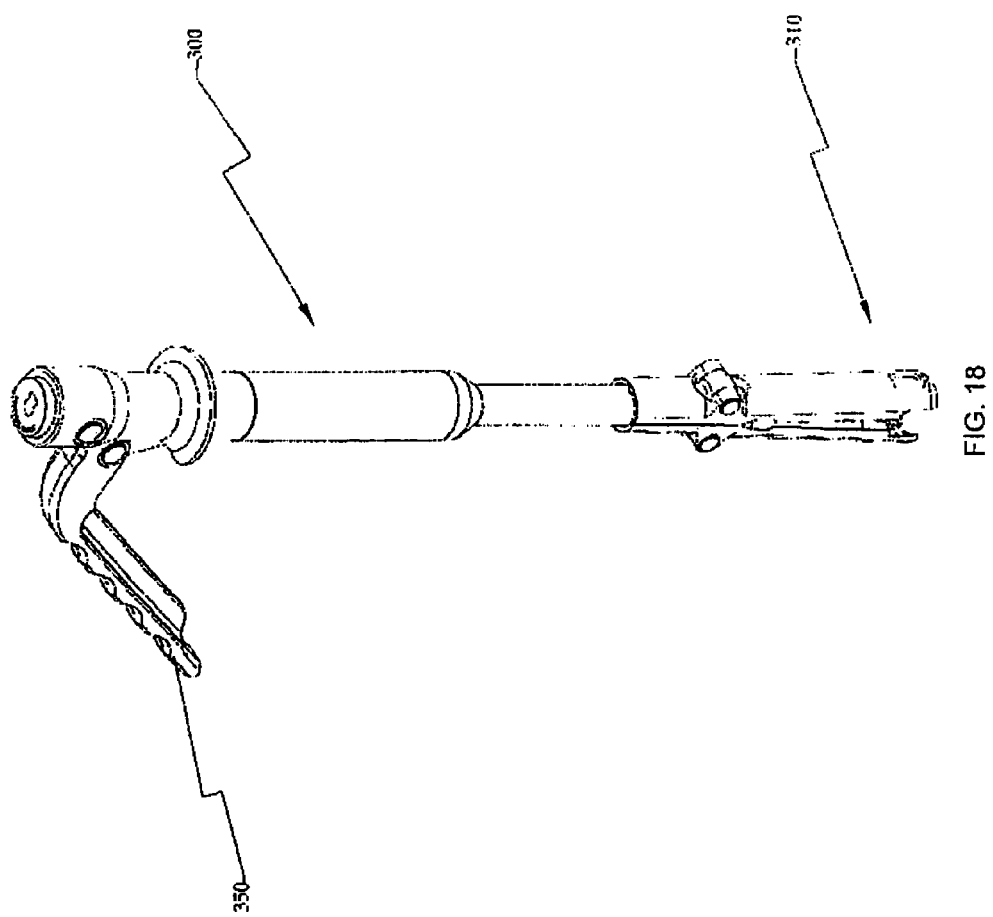

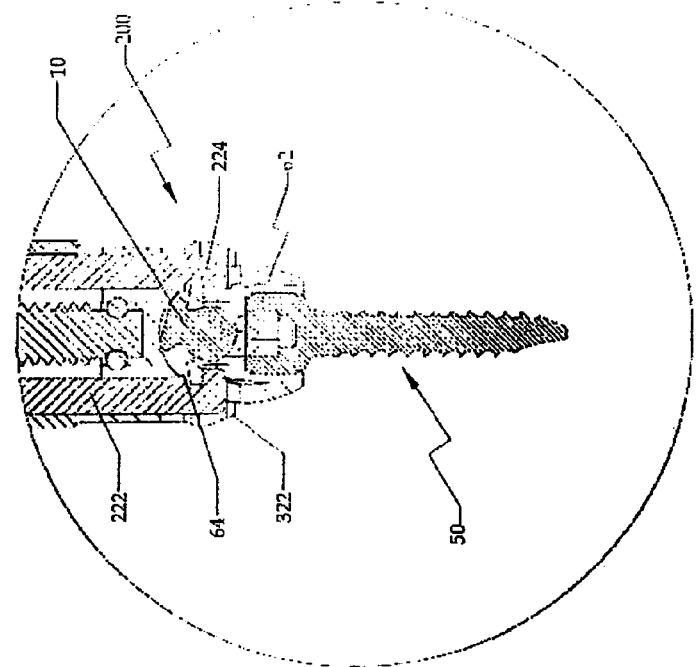
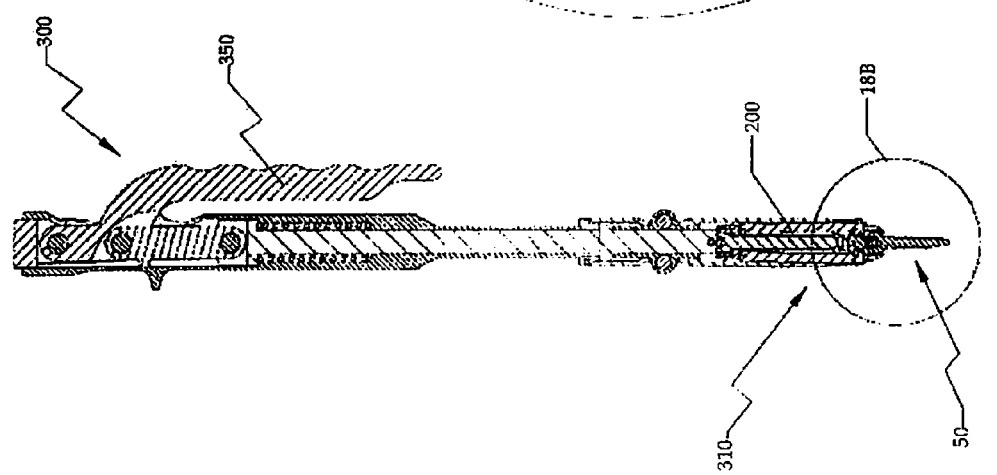
FIG. 18B
FIG. 18A

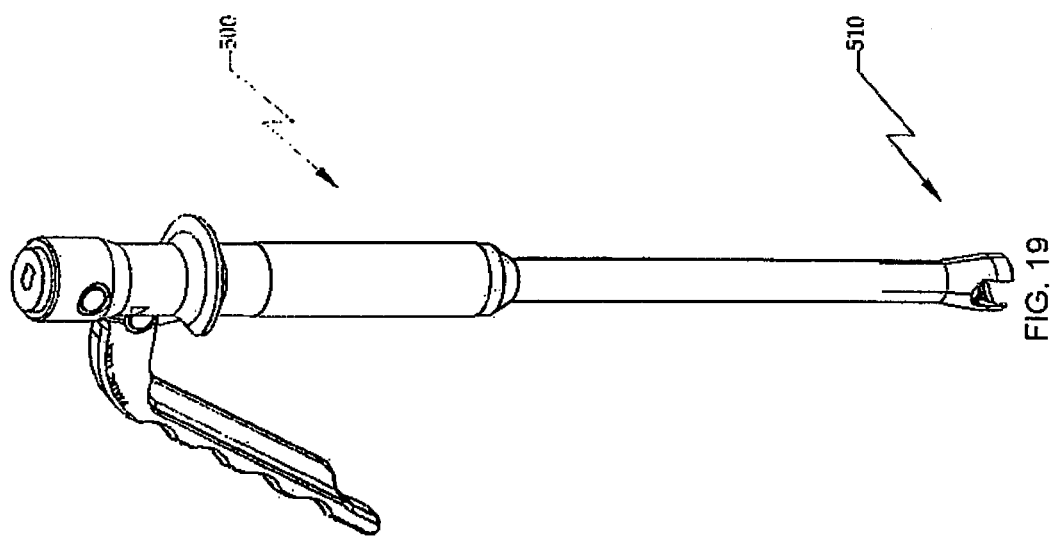

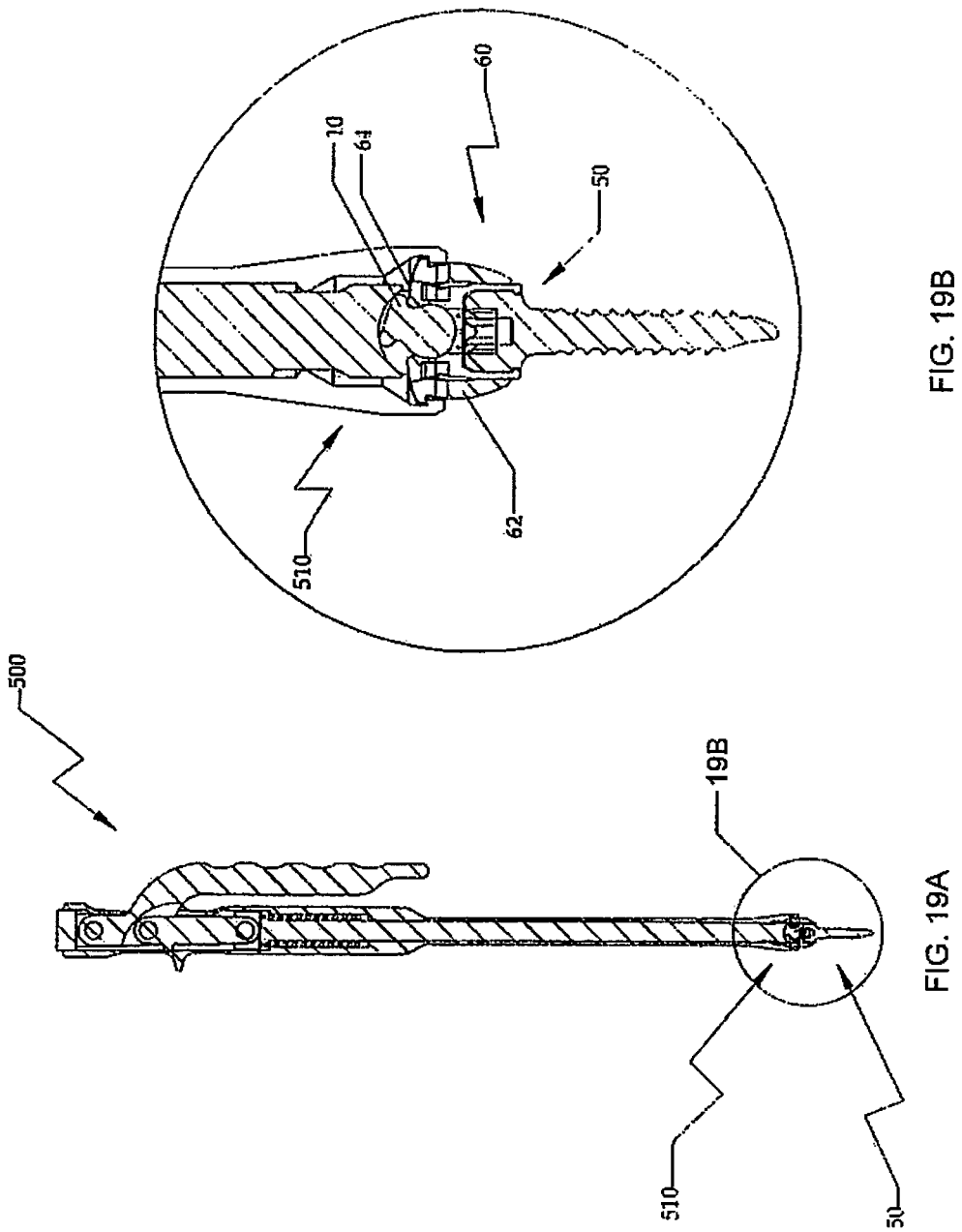

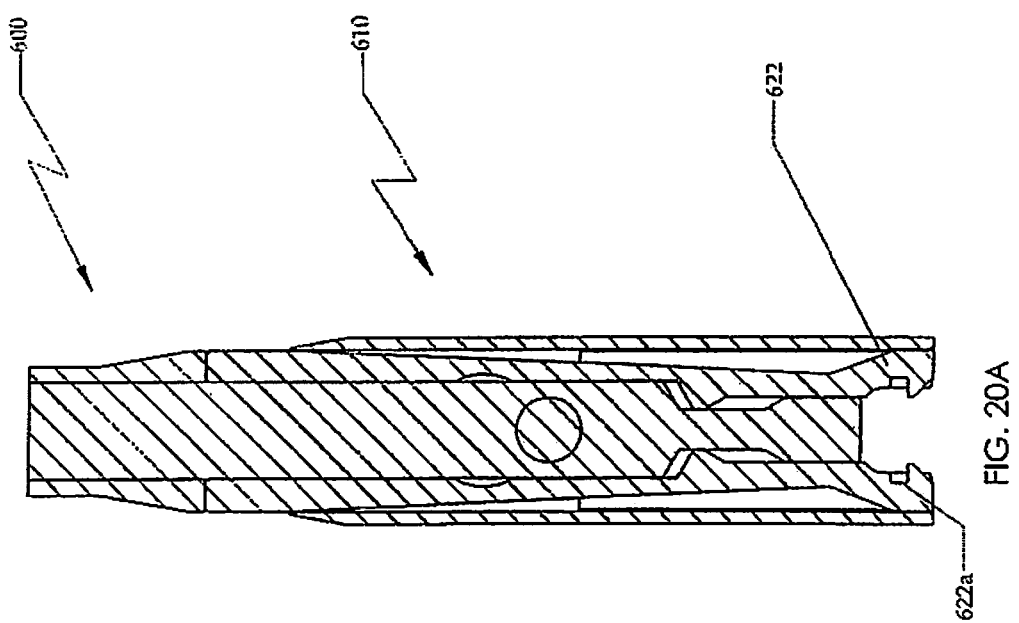

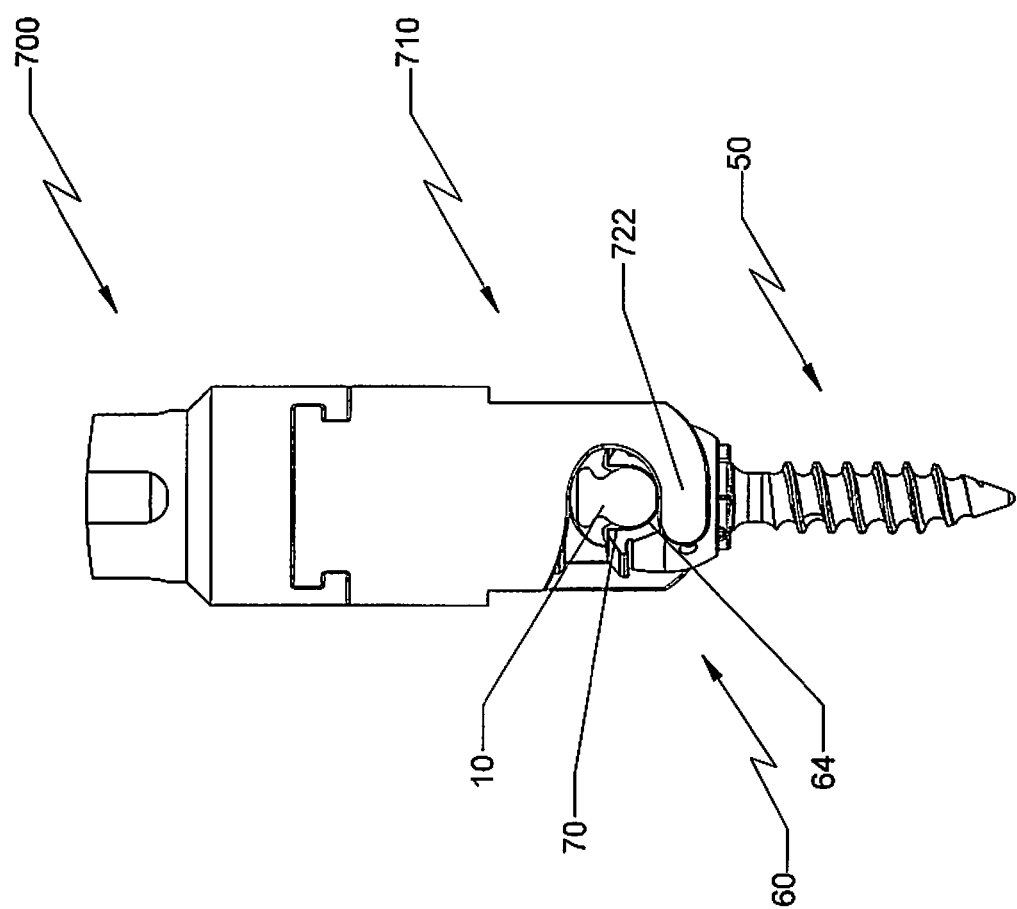

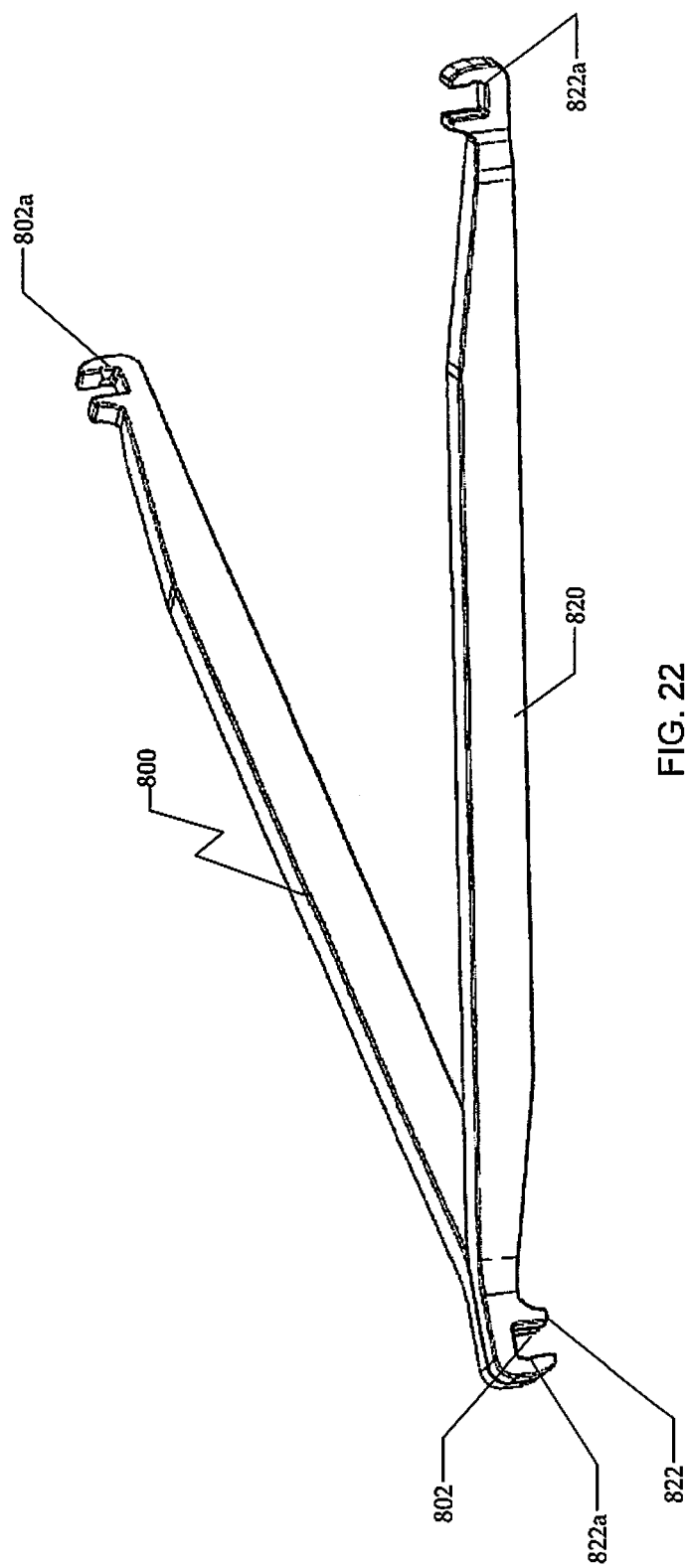

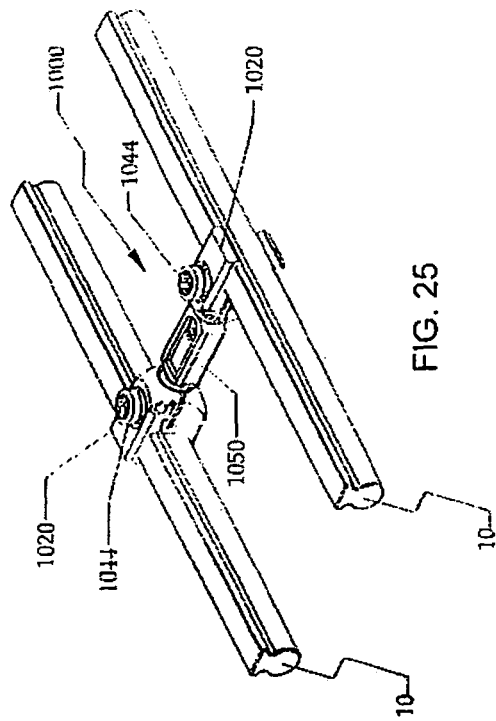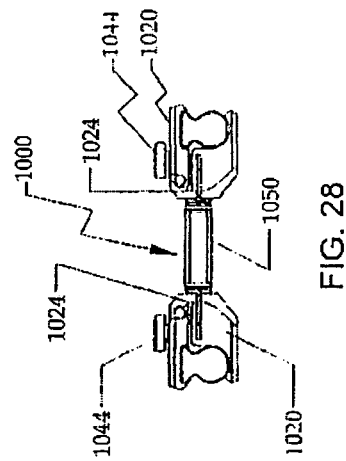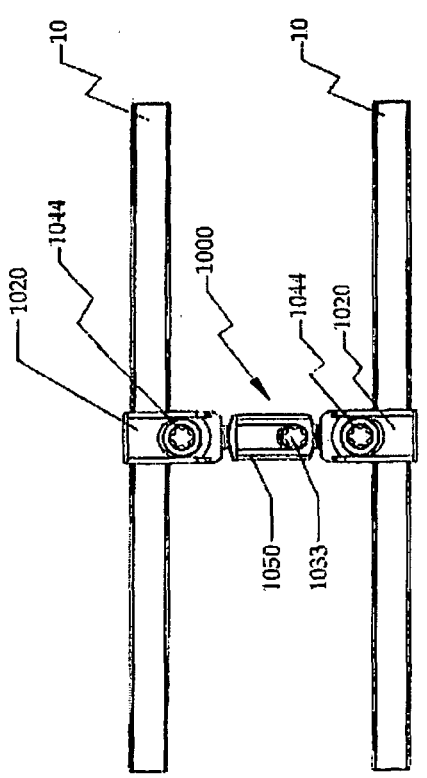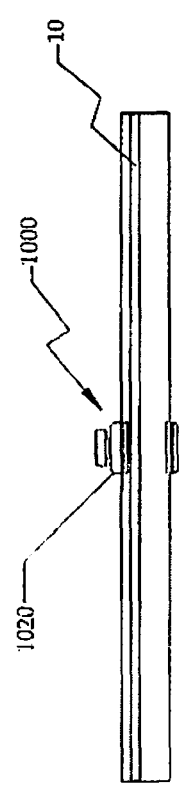
FIG. 25
FIG. 28
FIG. 26
FIG. 27

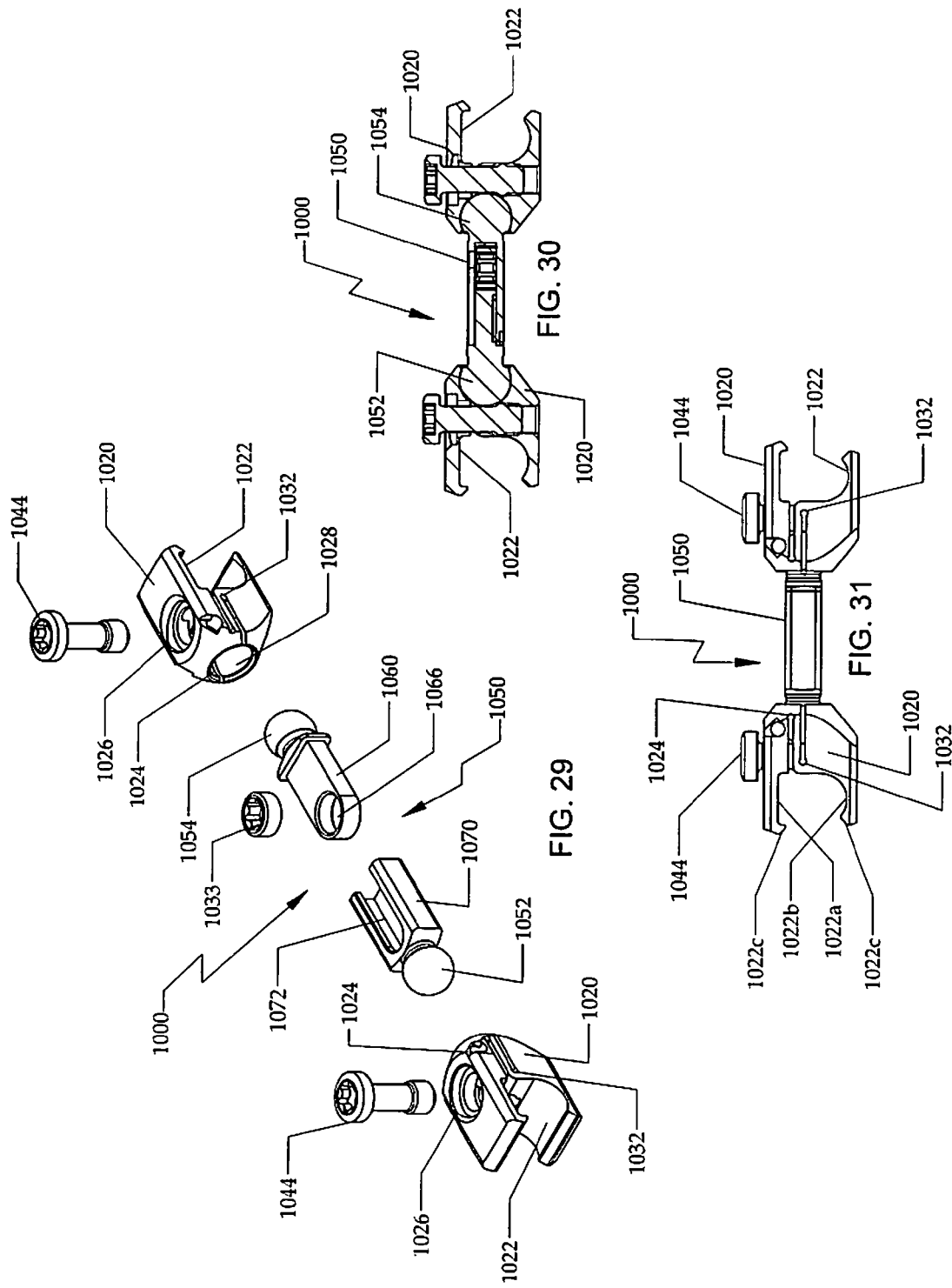

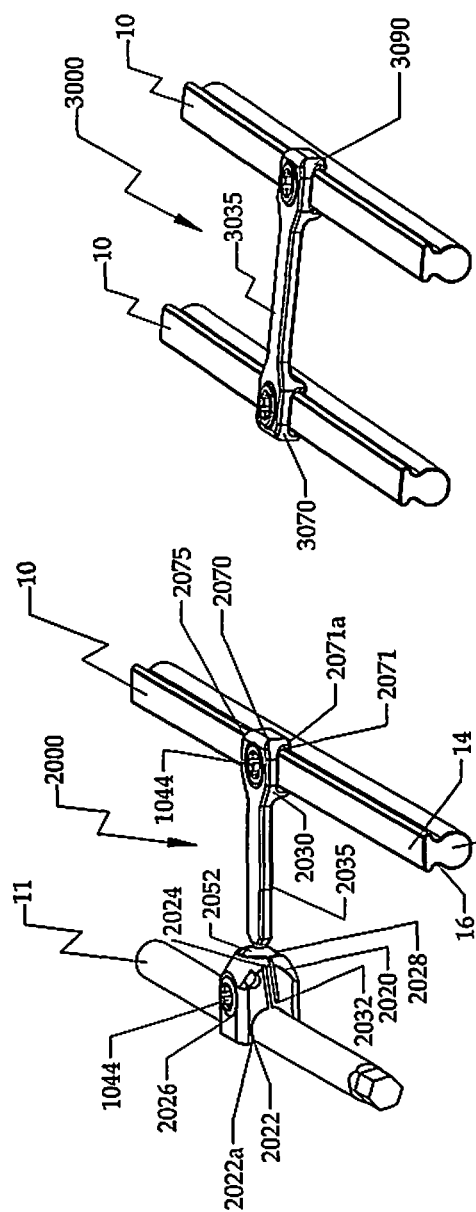

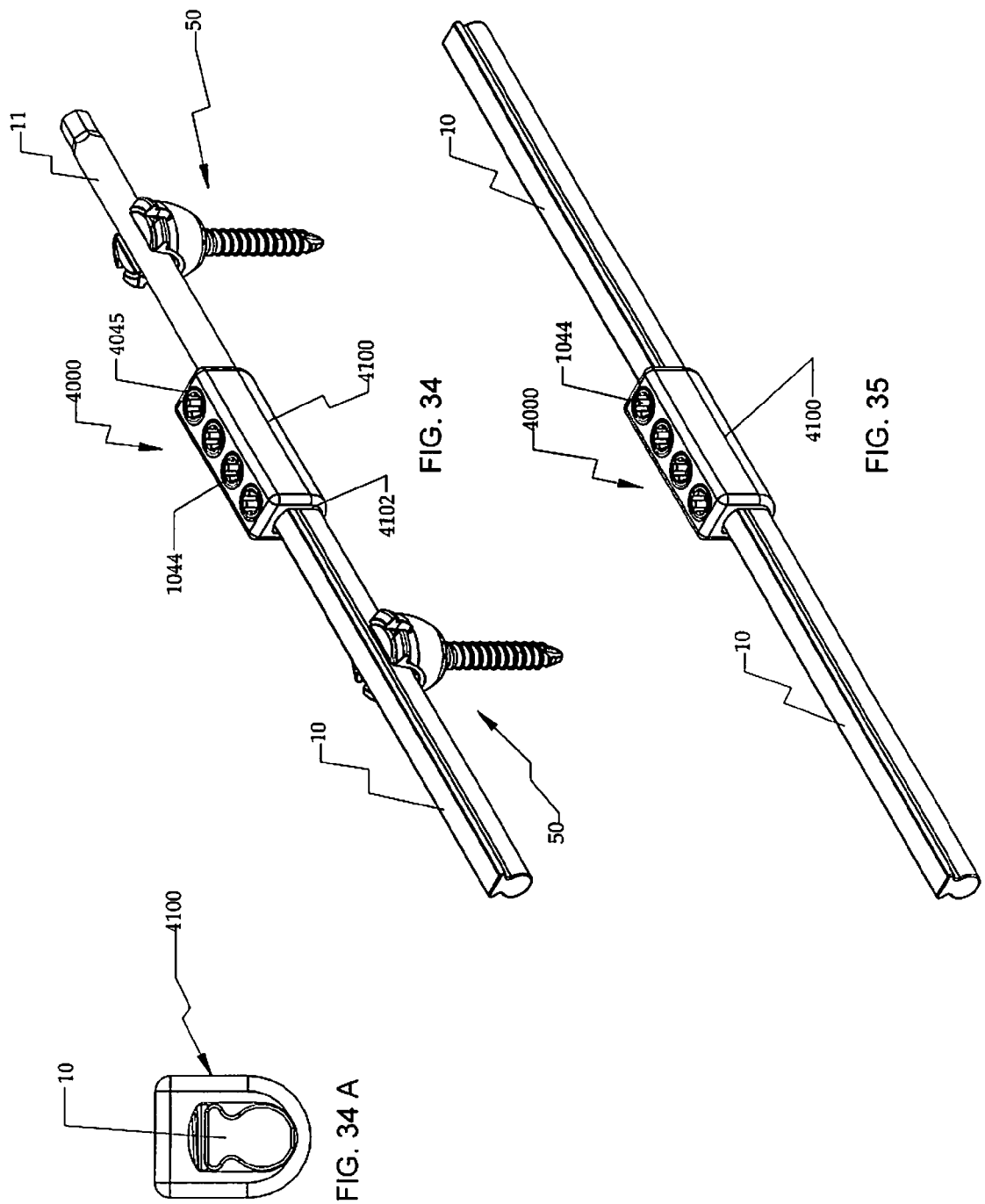

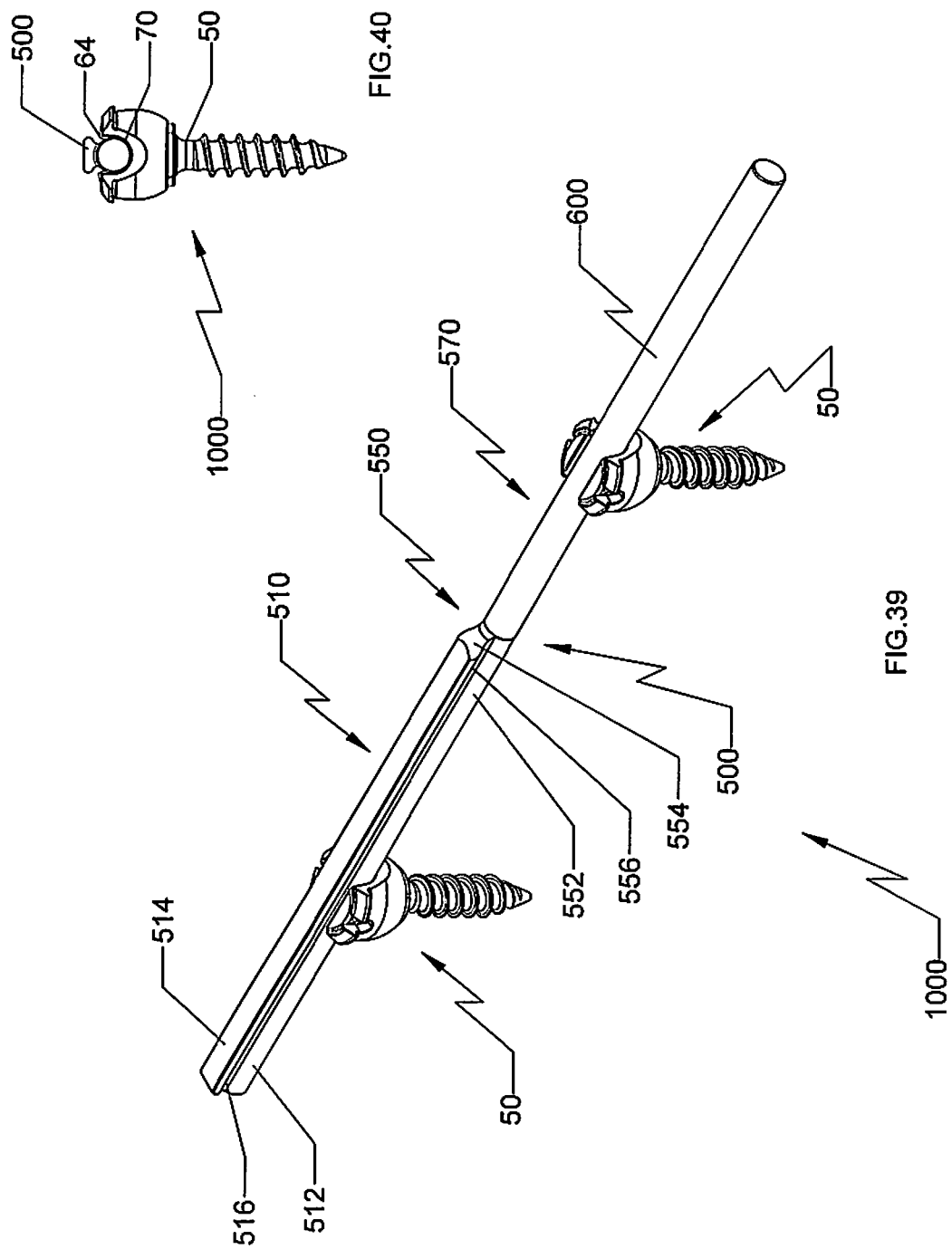

SPINE STABILIZATION SYSTEM

CROSS-REFERENCE TO RELATED APPLICATION

This application is a continuation-in-part of International Application No. PCT/US11/42127, filed on Jun. 28, 2011, which claims priority to, and the benefit of, U.S. Provisional Patent Application No. 61/359,028, filed on Jun. 28, 2010. The present application also claims priority to, and the benefit of, U.S. Provisional Patent Application No. 61/537,112, filed on Sep. 21, 2011. The entire contents of each of these prior applications are hereby incorporated by reference herein.

BACKGROUND

1. Technical Field

The present disclosure relates to orthopedic surgical devices, and more particularly, to a spinal stabilization system and a method of use therefor.

2. Background of Related Art

The spinal column is a complex system of bones and connective tissues that provide support for the human body and protection for the spinal cord and nerves. The adult spine is comprised of an upper and lower portion. The upper portion contains twenty-four discrete bones, which are subdivided into three areas including seven cervical vertebrae, twelve thoracic vertebrae and five lumbar vertebrae. The lower portion is comprised of the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases and types of injury, which restrict the range of motion of the spine or interfere with important elements of the nervous system. The problems include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases. When the disc has degenerated to the point of requiring removal, there are a variety of interbody implants that are utilized to take the place of the disc. These include interbody spacers, metal cages and cadaver and human bone implants. In order to facilitate stabilizing the spine and keeping the interbody in position, other implants are commonly employed, such as bone screws and rods. Depending on the pathology and treatment, a surgeon will select the appropriate spinal rod material and size, specifically, the cross-sectional diameter.

To meet the problem of providing a rigid pedicle screw and rod construct, especially for addressing the demands of stiff deformity corrections, larger rod constructs have been made to improve the strength of the screw and rod construct. Spinal rods are typically made of a titanium alloy. However when large deformity corrections need to be made, these rods are not always strong enough. Larger diameter stainless steel rods have been made for these applications, but a larger rod requires a larger mating screw head to contain the rod which in turn increases the profile of the construct. In addition, in order to reduce the likelihood of material incompatibility in vivo, the screw assembly also needs to be made of stainless steel to match the rod material, which is not a cost effective alternative.

Therefore, a need exists for a cost effective, rigid screw and rod construct that can still maintain a low profile, while maintaining the surgical correction.

SUMMARY

In accordance with an embodiment of the present disclosure, there is provided a spinal stabilization system including a connecting rod and a bone screw. The connecting rod includes an elongate round portion, an elongate head portion and a neck portion connecting the elongate round portion with the elongate head portion. The bone screw includes a housing portion and a screw shaft extending distally from the housing portion. The housing portion includes an inner housing and an outer housing slidably surrounding at least a portion of the inner housing. The inner housing defines a slot configured and dimensioned to releasably secure the elongate round portion of the connecting rod therein, wherein the outer housing is movable relative to the inner housing between an unlocked state in which the elongate round portion of the connecting rod is releasable from the slot defined in the inner housing and a locked state in which the connecting rod is secured in the slot.

The elongate head portion of the connecting rod may have a non-circular cross-section. In particular, the elongate head portion of the connecting rod may have a substantially rectangular cross-section. The neck portion of the connecting rod may have an arcuate profile. The neck portion and the elongate head portion of the connecting rod may be disposed proximal of the inner housing when the elongate round portion of the connecting rod is disposed in the slot defined in the inner housing. The connecting rod may be monolithically formed. The screw shaft may be fixed relative to the rod receiving portion, or may be coupled with the housing portion to permit uniaxial, monoaxial or polyaxial motion of the screw relative to the housing portion.

In accordance with another embodiment of the present disclosure, there is provided a spinal stabilization system including a connecting rod, a rod bending device, and a bone screw. The connecting rod includes an elongate round portion, an elongate head portion and a neck portion connecting the elongate round portion with the elongate head portion. The rod bending device includes an elongate body defining an aperture configured and dimensioned to receive therethrough the connecting rod in a single orientation. The bone screw includes a housing portion and a screw shaft extending distally from the housing portion. The housing portion includes an inner housing and an outer housing slidably surrounding at least a portion of the inner housing. The inner housing defines a slot configured and dimensioned to releasably secure the elongate round portion of the connecting rod therein, wherein the outer housing is movable relative to the inner housing between an unlocked state in which the elongate round portion of the connecting rod is releasable from the slot defined in the inner housing and a locked state in which the connecting rod is secured in the slot.

The rod bending device may further include a second aperture configured and dimensioned to receive the rod oriented orthogonal to the direction in which the first aperture receives the rod. Side walls defining the apertures may have an arcuate profile. The apertures may include a rounded portion and a non-circular portion. The non-circular portion of the apertures may have a substantially rectangular shape. The rod bending device may further include a third aperture configured and dimensioned to receive the rod oriented oppositely to the orientation in which the first aperture receives the rod.

In accordance with another aspect of the present disclosure, there is provided a method of stabilizing a spine. The method includes providing a spinal stabilization system including a connecting rod, a pair of rod bending devices, and a bone screw. In particular, the connecting rod includes an elongate round portion, an elongate head portion and a neck portion connecting the elongate round portion with the elongate head portion. The pair of rod bending devices each includes an elongate body defining at least one aperture therethrough, each aperture configured and dimensioned to receive therethrough the connecting rod in a single orientation. The bone screw includes a housing portion and a screw shaft extending distally from the housing portion. The housing portion includes an inner housing and an outer housing slidably surrounding at least a portion of the inner housing. The inner housing defines a slot configured and dimensioned to releasably secure the elongate round portion of the connecting rod therein, wherein the outer housing is movable relative to the inner housing between an unlocked state in which the elongate round portion of the connecting rod is releasable from the slot defined in the inner housing and a locked state in which the connecting rod is secured in the slot. The method further includes implanting a plurality of bone screws into a plurality of vertebral bodies, bending the connecting rod using the rod benders, inserting the connecting rod into the connecting rod slots in the plurality of bone screws, and locking the connecting rod in the connecting rod slots in the plurality of bone screws.

Bending the connecting rod may include inserting the connecting rod through an aperture in each of the pair of rod bending devices and applying leveraged force to the connecting rod through the handle members of the rod bending devices. Bending the connecting rod may include bending the connecting rod in an anterior-posterior orientation. Bending the connecting rod may include bending the connecting rod in a medial-lateral orientation. Providing multiple apertures in the rod bending devices facilitates bending the rod by permitting the rod to be oriented in various positions relative to the handles.

The pair of rod bending devices may include a plurality of apertures configured and dimensioned to receive therethrough the connecting rod. The plurality of apertures may be defined to receive the rod in different orientations. Bending the connecting rod may include inserting the connecting rod through the apertures of the pair of rod bending devices having different orientations and applying twisting force. In addition, inserting the connecting rod into the connecting rod slots in the bone screws may include positioning the elongate round portion of the connecting rod in the connecting rod slots in the plurality of bone screws. Bending the connecting rod may include bending the connecting rod to conform to a desired contour of the spine.

The method may further include orienting the plurality of bone screws to the contour of the connecting rod prior to locking the connecting rod in the connecting rod slots in the plurality of bone screws. In addition, locking the connecting rod in the connecting rod slots in the plurality of bone screws includes partially locking the connecting rod in the connecting rod slots.

In accordance with another aspect of the present disclosure, there is provided a kit for spinal surgery. The kit includes a connecting rod, a bone screw, a rod reduction device, a partial locker, and a quick locker. In particular, the connecting rod includes an elongate round portion, an elongate head portion and a neck portion connecting the elongate round portion with the elongate head portion. The bone screw includes a housing portion and a screw shaft extending distally from the housing portion. The housing portion includes an inner housing and an outer housing slidably surrounding at least a portion of the inner housing. The inner housing defines a slot configured and dimensioned to releasably secure the elongate round portion of the connecting rod therein, wherein the outer housing is movable relative to the inner housing between an unlocked state in which the elongate round portion of the connecting rod is releasable from the slot defined in the inner housing and a locked state in which the connecting rod is secured to the slot. The rod reduction device is configured and adapted for attachment to the housing portion of the bone screw to reduce the connecting rod into the slot defined in the inner housing. The partial locker is configured to move the outer housing relative to the inner housing to partially lock the connecting rod to the housing. The quick locker is configured to move the outer housing with respect to the connecting rod to fully lock the connecting rod to the housing.

In an embodiment, the partial locker may include a distal end portion configured and adapted to receive the reduction device while the reduction device remains operably engaged with the bone screw. In addition, the kit may further include an unlocker configured and adapted to move the outer housing of the bone screw relative to the inner housing and the connecting rod to fully unlock the connecting rod from the housing. The kit may also include a rod puller configured and adapted to selectively engage the connecting rod to enable the unseating of the connecting rod from within the slot of the inner housing of the bone screw.

In accordance with still another aspect of the present disclosure, there is provided a method of stabilizing a spine. The method includes providing a spinal stabilization system including a connecting rod, a bone screw, a rod reduction device, a partial locker, and a quick locker. In particular, the connecting rod includes an elongate round portion, an elongate head portion and a neck portion connecting the elongate round portion with the elongate head portion. The bone screw includes a housing portion and a screw shaft extending distally from the housing portion. The housing portion includes an inner housing and an outer housing slidably surrounding at least a portion of the inner housing. The inner housing defines a slot configured and dimensioned to releasably secure the elongate round portion of the connecting rod therein. The outer housing is movable relative to the inner housing between an unlocked state in which the elongate round portion of the connecting rod is releasable from the slot defined in the inner housing and a locked state in which the connecting rod is secured to the slot. The rod reduction device is configured and adapted for attachment to the housing portion of the bone screw to reduce the connecting rod into the slot defined in the inner housing. The partial locker is configured to move the outer housing relative to the inner housing to partially lock the connecting rod to the housing. The quick locker is configured to move the outer housing with respect to the connecting rod to fully lock the connecting rod to the housing. The method further includes implanting a plurality of bone screws into a plurality of vertebral bodies, inserting the elongated round portion of the connecting rod into the slots in the plurality of bone screws with the rod reduction device and locking the connecting rod in the slots in the plurality of bone screws.

In an embodiment, locking the connecting rod in the slots in the plurality of bone screws may include partially locking the connecting rod in the slots with the partial locker. In addition, locking the connecting rod in the slots in the plurality of bone screws may include fully locking the connecting rod in the slots with the quick locker.

In accordance with still yet another embodiment of the present disclosure, there is provided a spinal stabilization system including a pair of connecting rods and a cross connector assembly configured to couple the pair of connecting rods. Each connecting rod includes an elongate round portion, an elongate head portion and a neck portion connecting the elongate round portion with the elongate head portion. The cross connector assembly includes a pair of connectors each defining a recessed portion configured to secure one of the pair of connecting rods therein and an intermediate portion connecting the pair of connectors, wherein the recessed portion includes an arcuate wall configured to receive the elongate round portion of the connecting rod and an opposing non-circular wall configured to receive the elongate head portion of the connecting rod.

In an embodiment, each connector may define a slit configured to flex or enlarge the dimensions of the recessed portion to facilitate insertion of the connecting rod. The non-circular wall may have a substantially rectangular cross-section. The recessed portion may include a pair of opposing fingers to secure the connecting rod within the recessed portion. Furthermore, the intermediate portion may be retractable to enable adjustment of a length of the intermediate portion.

In another embodiment, the spinal stabilization system may further include a circular rod, wherein the arcuate wall of the recessed portion is configured to receive the circular rod therein.

In accordance with still yet another embodiment of the present disclosure, there is provided a spinal stabilization system including a pair of connecting rods and a cross-connector assembly configured to couple the pair of connecting rods. Each connecting rod includes an elongate round portion, an elongate head portion and a neck portion connecting the elongate round portion with the elongate head portion. The cross connector includes a pair of connectors each defining a recessed portion configured to secure one of the pair of connecting rods therein. The recessed portion is configured to receive the elongate head portion of the connecting rod. Each recessed portion defines a pair of fingers to secure the elongate head portion therebetween.

In an embodiment, the cross connector may be made of a relatively flexible material to provide a snap fit engagement with the elongate head portion.

In accordance with still yet another embodiment of the present disclosure, there is provided a spinal stabilization system including a connecting rod and a bone screw. The connecting rod includes a first portion and a second portion. The first portion includes an elongate round portion, an elongate head portion, and a neck portion connecting the elongate round portion with the elongate head portion. The second portion includes a circular rod. The circular rod is coupled to the elongate round portion. The bone screw includes a housing portion and a screw shaft extending distally from the housing portion. The housing portion includes an inner housing and an outer housing slidably surrounding at least a portion of the inner housing. The inner housing defines a slot configured and dimensioned to releasably secure the connecting rod therein, wherein the outer housing is movable relative to the inner housing between an unlocked state in which the connecting rod is releasable from the slot defined in the inner housing and a locked state in which connecting rod is secured to the slot.

In an embodiment, the connecting rod may further include a transition portion connecting the first and second portions. The transition portion may be longitudinally tapered. In particular, the transition portion may include a first end having a cross section substantially identical to a cross section of the first portion and a second end having a cross section substantially identical to the cross section of the second portion. In addition, the first end may be adjacent the first portion and the second end may be adjacent the second portion. In another embodiment, the connecting rod may be monolithically formed.

BRIEF DESCRIPTION OF THE DRAWINGS

The foregoing and other features of the present disclosure will become apparent to one skilled in the art to which the present disclosure relates upon consideration of the following description of the disclosure with reference to the accompanying drawings, wherein:

FIG. 5A is an end, cross-sectional view of the spinal stabilization system of FIG. 1 in a locked position;

FIG. 12A is a side view of a rod bender device for use with the spinal stabilization system of FIG. 1;

FIG. 12B is a side cross-sectional view of the area of detail indicated in FIG. 12A;

FIG. 18 is a perspective view of a partial locker for use with the spinal stabilization system of FIG. 1;

FIG. 18A is a longitudinal cross-sectional view of the partial locker of FIG. 18 operatively connected to a screw and a connecting rod;

FIG. 18B is a longitudinal cross-sectional view of the area of detail indicated in FIG. 18A;

FIG. 19 is a perspective view of a quick locker for use with the spinal stabilization system of FIG. 1;

FIG. 19A is a longitudinal cross-sectional view of the quick locker of FIG. 19 operatively connected to a screw and a connecting rod;

FIG. 19B is a longitudinal cross-sectional view of the area of detail indicated in FIG. 19A operatively connected to a screw and a connecting rod;

FIG. 20A is a partial, longitudinal cross-sectional view of the unlocker of FIG. 20;

FIG. 21A is a partial, side view of the rod puller of FIG. 21 operatively connected to a screw and a connecting rod;

FIGS. 22-24 are perspective views of various rod benders for use with the spinal stabilization system of FIG. 1;

FIG. 25 is a perspective view of a cross connector assembly for use with the spinal stabilization system of FIG. 1;

FIG. 26 is a top view of the cross connector assembly of FIG. 25;

FIG. 27 is a side view of the cross connector assembly of FIG. 25;

FIG. 28 is an end view of the cross connector assembly of FIG. 25;

FIG. 29 is an exploded perspective view of the cross connector assembly of FIG. 25 with parts separated;

FIG. 30 is an end, cross-sectional view of the cross connector assembly of FIG. 25;

FIG. 31 is an end view of the cross connector assembly of FIG. 25;

FIGS. 32 and 33 are perspective views of other cross connector assemblies for use with the spinal stabilization system of FIG. 1;

FIG. 34 is a perspective view of an axial connector illustrating use with different connecting rods;

FIG. 34A is a side view of the axial connector of FIG. 34 operatively coupling different connecting rods;

FIG. 35 is a perspective view of the axial connector of FIG. 34 illustrating use with the connecting rods of FIG. 1;

FIG. 36A is a side view of the offset connector of FIG. 36 operatively coupling different connecting rods;

FIG. 37A is a side view of the offset connector of FIG. 37 operatively coupling the connecting rods of FIG. 1;

FIG. 38A is a side view of the spinal hook of FIG. 38 operatively coupled with the connecting rod of FIG. 7;

FIG. 39 is a perspective view of a spinal stabilization system in accordance with yet another embodiment of the present disclosure; and FIG. 40 is an end view of the spinal stabilization system of FIG. 39.

DETAILED DESCRIPTION OF EMBODIMENTS

Figure 1:
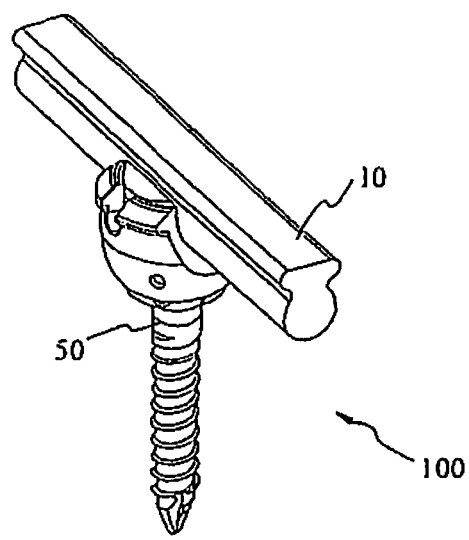
FIG. 1 is a perspective view of a spinal stabilization system in accordance with an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In addition, the term "cephalad" is used in this application to indicate a direction toward a patient's head, while the term "caudad" indicates a direction toward the patient's feet. Further still, for the purposes of this application, the term "medial" indicates a direction toward the middle of the body of the patient, while the term "lateral" indicates a direction toward a side of the body of the patient, i.e., away from the middle of the body of the patient. The term "posterior" indicates a direction toward the patient's back, while the term "anterior" indicates a direction toward the patient's front. In the following description, well-known functions or constructions are not described in detail to avoid obscuring the present disclosure in unnecessary detail.

With reference to FIGS. 1-4, an embodiment of the present disclosure is shown generally as a spinal stabilization system 100. Spinal stabilization system 100 includes at least one bone screw 50 and a connecting rod 10 releasably secured to bone screw 50. Bone screw 50 is a multi-planar taper lock screw that enables manipulation of a screw shaft 52 about multiple axes, whereby bone screw 50 is capable of securing connecting rod 10 with bone screws 50 on multiple vertebral bodies that are aligned in the spinal column on different planes due to the natural curvature of the spine. However, it is also envisioned that bone screws 50 may be, for example, fixed angle screw, uniplanar screws or monoaxial taper lock screws.

One suitable taper lock screw is commercially available from K2M, Inc. (Leesburg, Va.) under the trade name MESA™. In addition, suitable multi-planar taper lock screws are shown and described in U.S. Patent Application Publication 2008/0027432 and in U.S. Patent Application Publication 2007/0093817, both of which are herein incorporated by reference in their entireties. It is contemplated that other types of screws such as, e.g., a fixed screw in which the head of the screw has no movement relative to the screw shaft, a monoaxial screw such as that disclosed in U.S. Patent Application Publication 2009/0105716, and a uni-axial screw such as that disclosed in U.S. Patent Application Publication 2009/0105769 may be utilized. Suitable mono-axial and uni-axial screws are also commercially available under the trade name MESA™.

Figure 4:
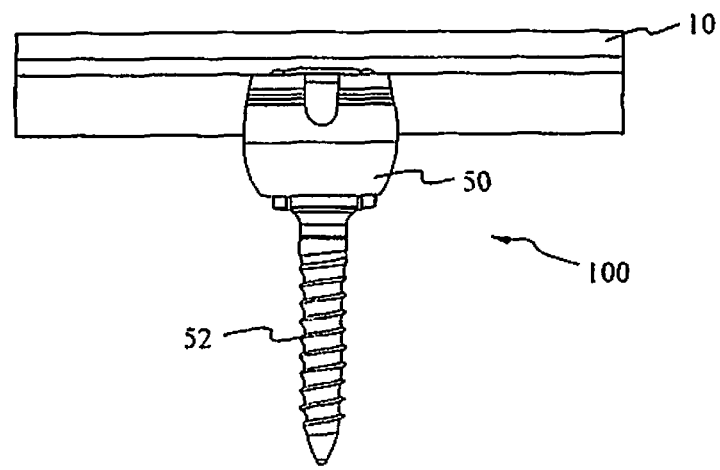
FIG. 4 is a side view of the spinal stabilization system of FIG. 1.
Figure 5:
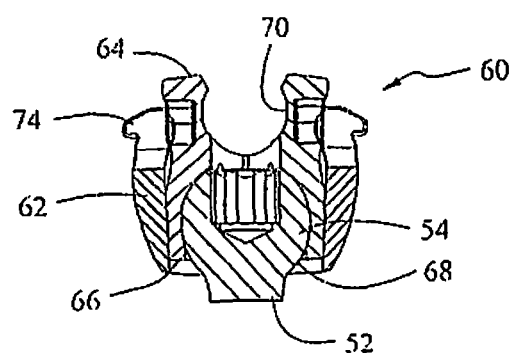
FIG. 5 is a partial cross-sectional view of a taper lock screw of the spinal stabilization system of FIG. 1 shown in an unlocked position to receive a rod.

With reference now to FIGS. 4, 5 and 5A, a suitable multi-planar taper lock bone screw 50 includes a dual layered housing 60 and screw shaft 52 having a spherically configured screw head 54 rotatably coupled with housing 60. In particular, dual layered housing 60 includes an outer housing 62 and an inner housing 64. Outer housing 62 can be selectively positioned relative to inner housing 64 to fully lock screw head 54 and connecting rod 10 in position within inner housing 64 (see FIG. 4) or alternatively to selectively partially lock screw head 54 and/or connecting rod 10 in position while permitting a sliding and/or rotating motion of the connecting rod 10 relative to screw head 54, and the screw head 54 relative to bone screw 50, respectively. Specifically, outer housing 62 is configured such that at least a portion of an inner surface of outer housing 62 is capable of sliding over a portion of an outer surface of inner housing 64 in upward and downward directions along the longitudinal axis of bone screw 50. When outer housing 62 is slid upward in relation to inner housing 64 an inner surface of outer housing 62 causes inner housing 64 to impart compressive force radially inward to secure connecting rod 10 at least partially disposed therein.

With continued reference to FIG. 5, inner housing 64 defines a connecting rod slot 70 that is configured and dimensioned to accommodate the connecting rod geometry contemplated by the present disclosure, and to retain connecting rod 10 in inner housing 64 without impairing the locking ability of bone screw 50. Specifically, an elongate rounded section 12 of connecting rod 10 is releasably secured in connecting rod slot 70 of inner housing 64, as will be discussed in detail below. The term "rounded" in elongate rounded section 12 refers to a portion of connecting rod 10 having a generally circular/arcuate cross-section that is received in bone screw 50. In particular, inner walls that define connecting rod slot 70 imparts compressive force to connecting rod 10 disposed in connecting rod slot 70, whereby the inner walls serve to securely lock and hold connecting rod 10 in its relative position to inner housing 64. This required forced is provided by the operational engagement of a locking device (not shown) with bone screw 50 that results in an upward sliding motion of outer housing 62 relative to inner housing 64.

Inner housing 64 further defines a screw head articulation recess 66 in a lower portion of inner housing 64. The interior surface of screw head articulation recess 66 has a complementary surface configuration to the generally spherical shape of screw head 54 to facilitate multi-planar rotational articulation of screw head 54 within articulation recess 66. The lower-most portion of inner housing 64 defines a screw shaft exit portal 68 that is sized small enough to retain the spherical screw head 54 within screw head articulation recess 66, but that is large enough to allow multi-directional movement of screw shaft 52 that extends exterior to inner housing 64.

Outer housing 62 includes a receiving element configured to facilitate grasping of bone screw 50 by a locking and/or unlocking instrument (not shown) that can insert and lock connecting rod 10 securely into place in bone screw 50 or selectively unlock connecting rod 10 from bone screw 50 using complementarily designed unlocking instruments. The receiving element is a proximally located annular flange 74 radially extending from the upper portion of the outer surface of outer housing 62.

With reference back to FIGS. 1-4, connecting rod 10 is configured and dimensioned to be selectively and releasably secured to bone screw 50. Connecting rod 10 is defined by an elongate body of a particular length. The elongate body is made of a biocompatible material such as Titanium (Ti-CP) and its alloys (e.g., Ti-6Al-4V), Cobalt-Chrome Alloy (CoCr) or Stainless Steel (SS).

Figure 6:
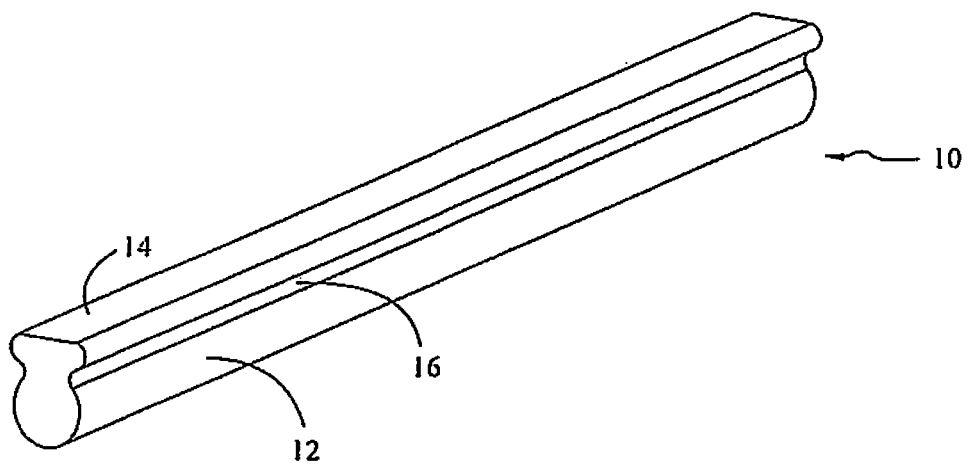
FIG. 6 is a perspective view of a connecting rod of the spinal stabilization system of FIG. 1.
Figure 7:
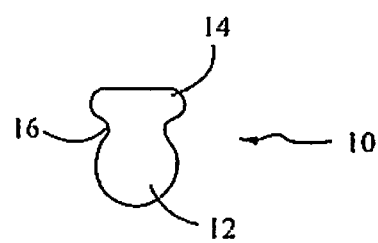
FIG. 7 is an end view of the connecting rod of FIG. 6.
Figure 8:
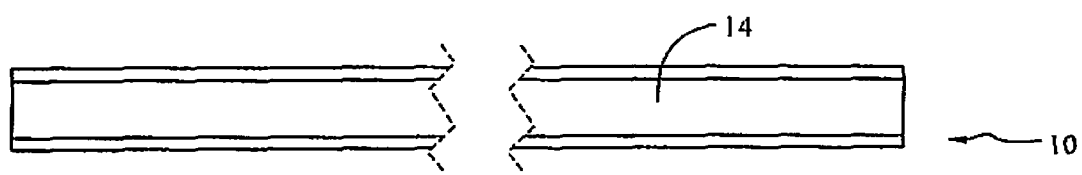
FIG. 8 is a top view of the connecting rod of FIG. 6.
Figure 9:
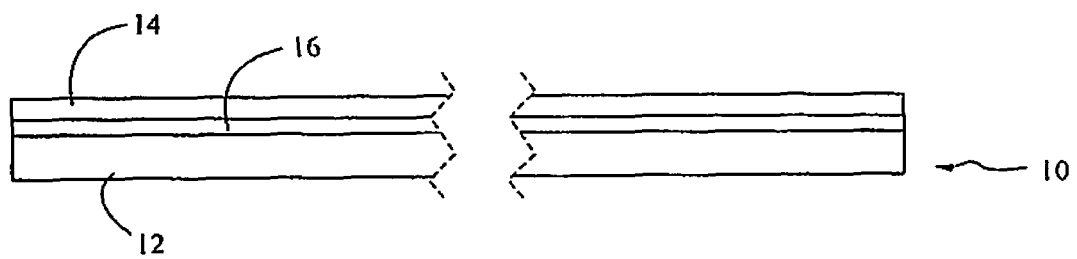
FIG. 9 is a side view of the connecting rod of FIG. 6.

With reference to FIGS. 6 and 7, the elongate body of connecting rod 10 includes an elongate rounded section 12 having a substantially circular cross-section (see FIG. 7), an elongate head portion 14, and a neck portion 16 that connects and transitions elongate rounded section 12 into elongate head portion 14, thereby providing reduced stress concentration along the elongate body of connecting rod 10. Neck portion 16 has dimensions that are smaller than those of elongate rounded section 12 and elongate head portion 14. The neck portion may define a pair of concave sides joining the elongate head portion to the elongate rounded portion, so that the concave sides provide clearance for the taper lock screw housings. The elongate body of connecting rod 10 may be monolithically formed as a unitary construct. For example, connecting rod 10 may be machined from a single piece of bar stock.

With reference now to FIGS. 6 to 9, elongate head portion 14 may have a non-circular cross-section. As shown, elongate head portion 14 has a substantially rectangular cross-section having suitable dimensions of, for example, about 6 mm×about 1 mm (0.246 in.×0.039 in.). However, it is envisioned that elongate head portion 14 may have a cross-section that is substantially square, elliptical or any other shape to add rigidity to round section 12 of connecting rod 10.

Figure 2:
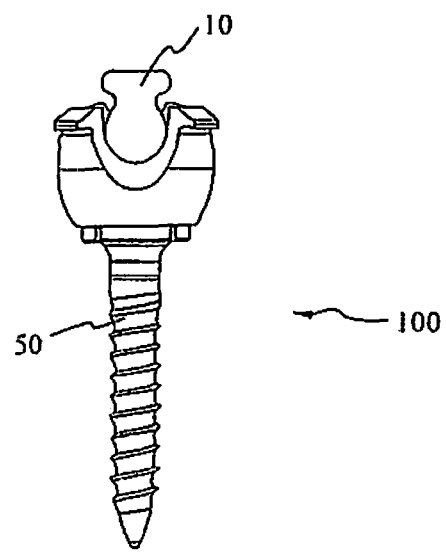
FIG. 2 is an end view of the spinal stabilization system of FIG. 1.
Figure 3:
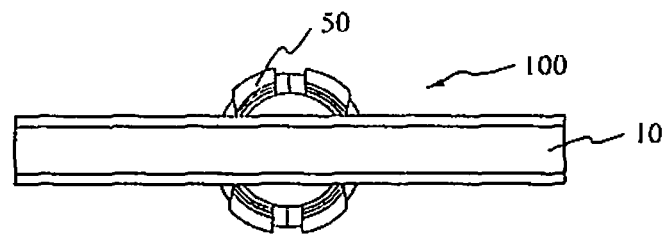
FIG. 3 is a top view of the spinal stabilization system of FIG. 1.

With particular reference back to FIGS. 5 and 6, elongate rounded section 12 of connecting rod 10 is configured and dimensioned to be received in connecting rod slot 70 of inner housing 64 (see FIG. 2). For example, round section 12 of connecting rod 10 may have a standard diameter of, for example, about 5.5 mm, suitable to mate with connecting rod slot 70. Bone screw 50 may be positioned at any desired point along the elongate body of connecting rod 10. When connecting rod 10 is secured to bone screw 50, neck portion 16 of connecting rod 10 is disposed at the top of bone screw 50 (FIG. 2) and does not interfere with the interaction between connecting rod 10 and bone screw 50. Furthermore, elongate head portion 14 of connecting rod 10 is disposed above the top of taper lock screw 50. While elongate head portion 14 is disposed above elongate rounded section 12, head portion 14 does not appreciably increase the height profile of the screw-rod combination.

Figure 10:
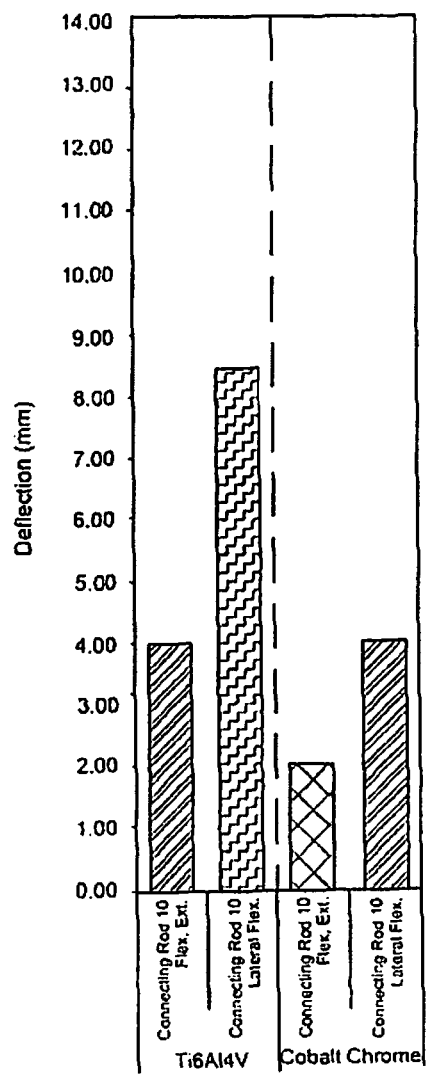
FIG. 10 is a graph illustrating deflection of the connecting rod of FIG. 6.

Connecting rod 10 affords greater strength and rigidity in comparison with ordinary circular rods with comparable dimensions. With reference now to FIG. 10, connecting rods 10 made of different materials were placed under cantilever loading and were analyzed under Finite Element Analysis (FEA), wherein each rod sample was 100 mm in length. The distal end was fixed while the proximal end was subject to 200 N of force. Connecting rod 10 lacks radial symmetry. Accordingly, the graph differentiates deflection of connecting rod 10 between cantilever loading in flexion/extension and lateral bending.

For example, placing a circular rod formed from a titanium alloy (e.g. Ti-6Al-4V) under the same loading conditions as connecting rod 10 in FIG. 10 results in a deflection of about 13.4 mm for a rod diameter of 5.5 mm and a deflection of about 5.00 mm for a rod with a diameter of 7.00 mm. A stainless steel rod placed under the same loading conditions results in a deflection of about 8.00 mm for a rod diameter of 5.5 mm and a deflection of about 3.00 mm for a rod diameter of 7.00 mm. A rod formed from a cobalt chrome alloy under the same loading conditions has a deflection of about 6.8 mm for a rod diameter of 5.5 mm and a deflection of about 2.8 mm for a rod diameter of 7.00 mm.

Figure 11:
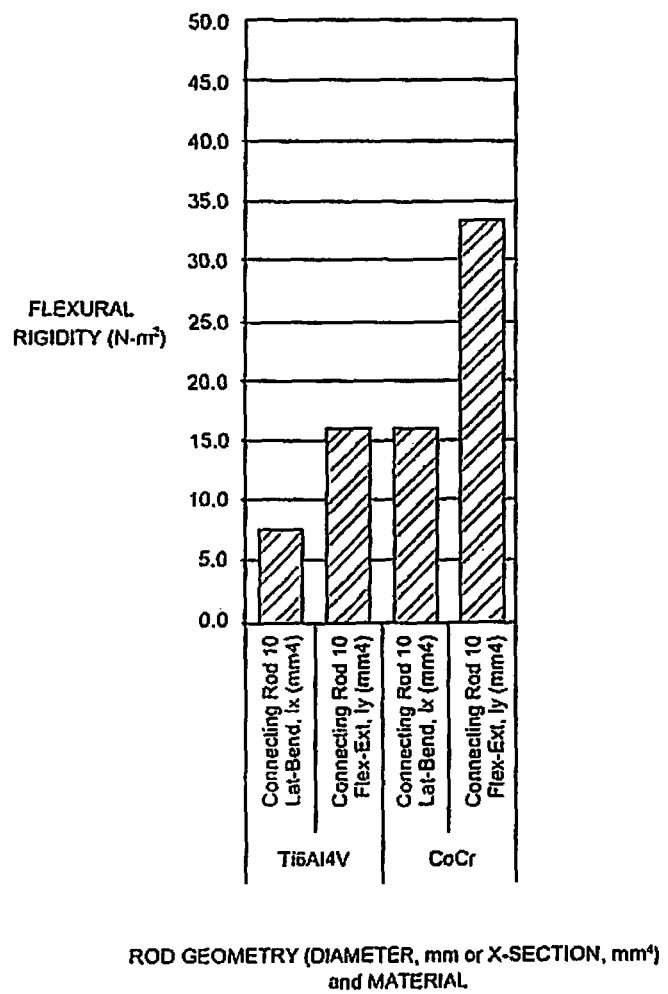
FIG. 11 is a graph illustrating flexural rigidity of the connecting rod of FIG. 6.

Flexural rigidity of connecting rod 10 is shown in FIG. 11. For example, circular rods made of a titanium alloy (e.g. Ti-6Al-4V) placed under the same loading conditions as connecting rod 10 in FIG. 11 have flexural rigidity of about 5.01 N-m$^2$ for a rod diameter of 5.5 mm and 23.5 N-m$^2$ for a rod diameter of 8.00 mm. Circular rods made of stainless steel placed under the same loading conditions have flexural rigidity of about 9.0 N-m$^2$ for a diameter of 5.5 mm and 40.01 N-m$^2$ for a rod diameter of 8.00 mm. Circular rods made of cobalt chrome alloy placed under the same loading conditions have flexural rigidity of about 10.1 N-m$^2$ for a rod diameter of 5.5 mm and 47.0 N-m$^2$ for a rod diameter of 8.00 mm.

Connecting rod 10 provides a greater stiffness and rigidity than circular rods having comparable dimensions in various materials. As such, connecting rod 10 and bone screw 50 construct affords greater rigidity and strength without increased bulk and profile. In addition, such construct, as shown, does not require any design changes to taper lock screw 50, and thus advantageously provides efficiency of manufacture and inventory.

Figure 13:
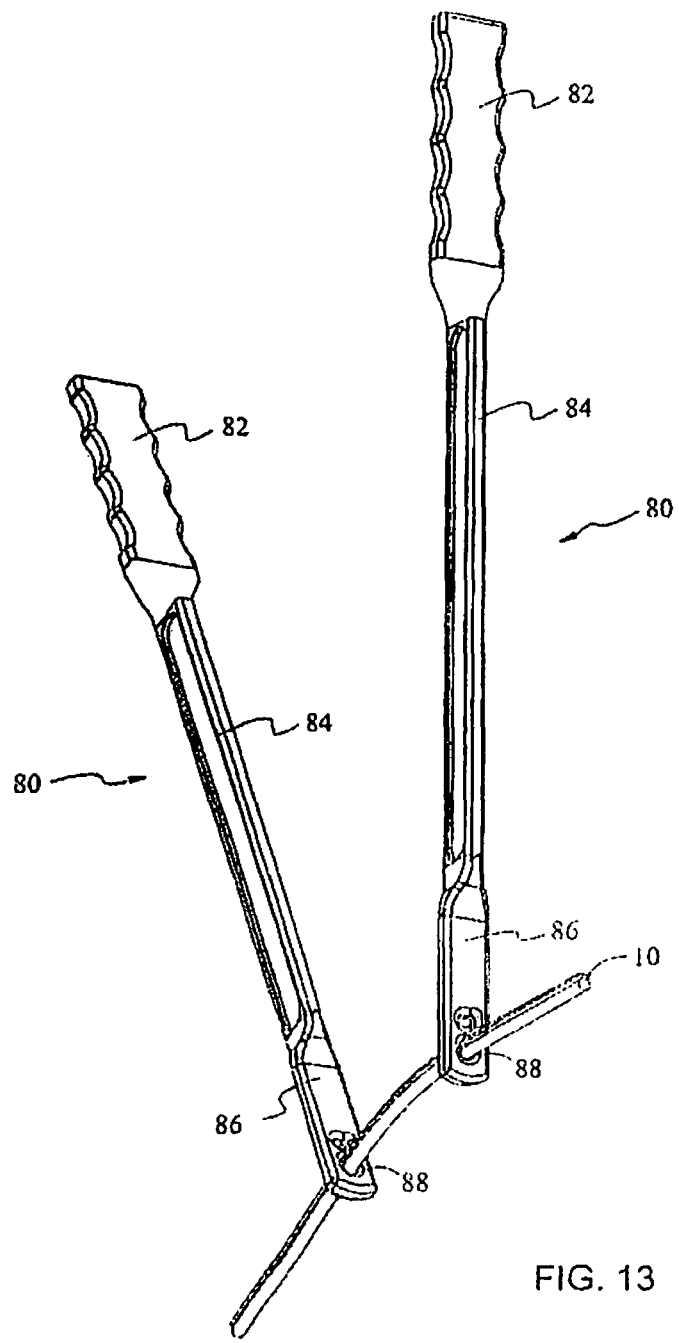
FIG. 13 is a perspective view of a pair of rod bender devices of FIG. 12A having the connecting rod of FIG. 6 inserted therethrough.
Figure 14:
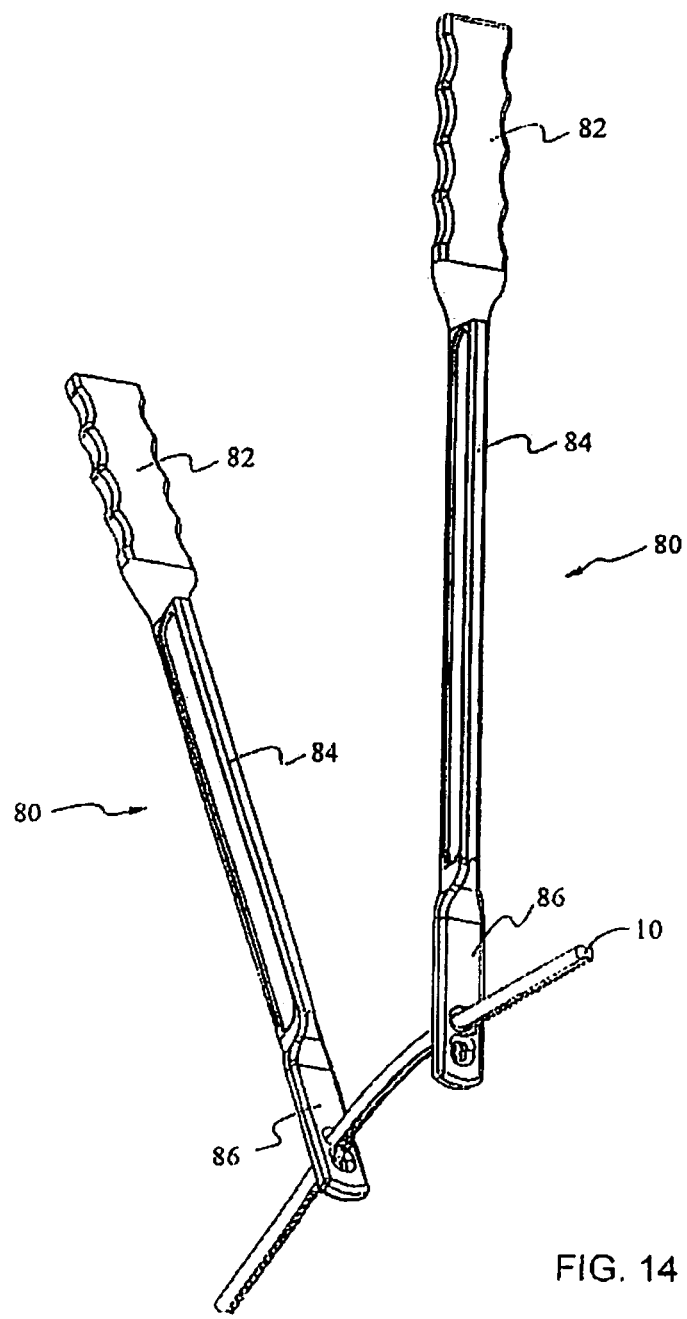
FIG. 14 is a perspective view of the pair of rod bender devices of FIG. 13 having the connecting rod of FIG. 6 inserted therethrough in a different orientation.

With reference now to FIGS. 12 to 14, spinal stabilization system 100 may further include rod bender devices 80. Each rod bender devices 80 define matching apertures 88 configured to receive and hold at least a portion of connecting rod 10 therein. Rod bender device 80 includes a handle member 82, an elongate body 84 extending distally from handle portion 82, and an engaging portion 86 coupled to elongate body 84. Elongate body 84 is coupled or formed with handle member 82 and engaging portion 86 so as to reduce stress concentration. Handle member 82 may contain scalloped sections to facilitate gripping by the user. Elongate body 84 may have a rectangular cross-section and may define a cavity along the length thereof to reduce the weight of device. Engaging portion 86 defines at least one aperture 88 adapted and dimensioned to receive therethrough connecting rod 10. In particular, inner walls that define aperture 88 are configured to permit insertion of connecting rod 10 through aperture 88 in a single orientation with respect to such aperture.

Aperture 88 has an arcuate end wall 88a configured to engage elongate rounded section 12 of connecting rod 10, an opposite substantially straight end wall 88b configured to engage the substantially flat portion of elongate head portion 14 of connecting rod 10, and connecting side walls 88c connecting arcuate end wall 88a and the substantially straight end wall 88b. In this manner, connecting rod 10 is inserted into each aperture 88 in a single orientation. Thus, in order to accommodate insertion of connecting rod in aperture 88 in various orientations, a plurality of apertures 88 is defined in engaging portion 86 in different orientations, as shown in FIG. 12A-12B. For example, the pair of apertures 88 defined in engaging portion 86 is oriented at a 90-degree angle, whereby the rectangular portions of apertures 88 are substantially orthogonal to each other. In this manner, the user can bend connecting rod 10 in both an anterior-posterior orientation and a medial-lateral orientation. It is also contemplated that connecting rod 10 may be inserted in non-corresponding apertures 88 in rod bender devices 80 to facilitate twisting of connecting rod 10, if necessary or desired.

The length of elongate body 84 is, for example, 18 inches. However, the length of elongate body 84 may be tailored to meet the needs of the surgical application to provide a suitable long moment arm necessary to provide the user a mechanical advantage to bend connecting rod 10. In addition, it is also envisioned that elongate body 84 may be a hollow tubular member and/or define lightening holes to reduce the weight of device 80.

Figure 16A:
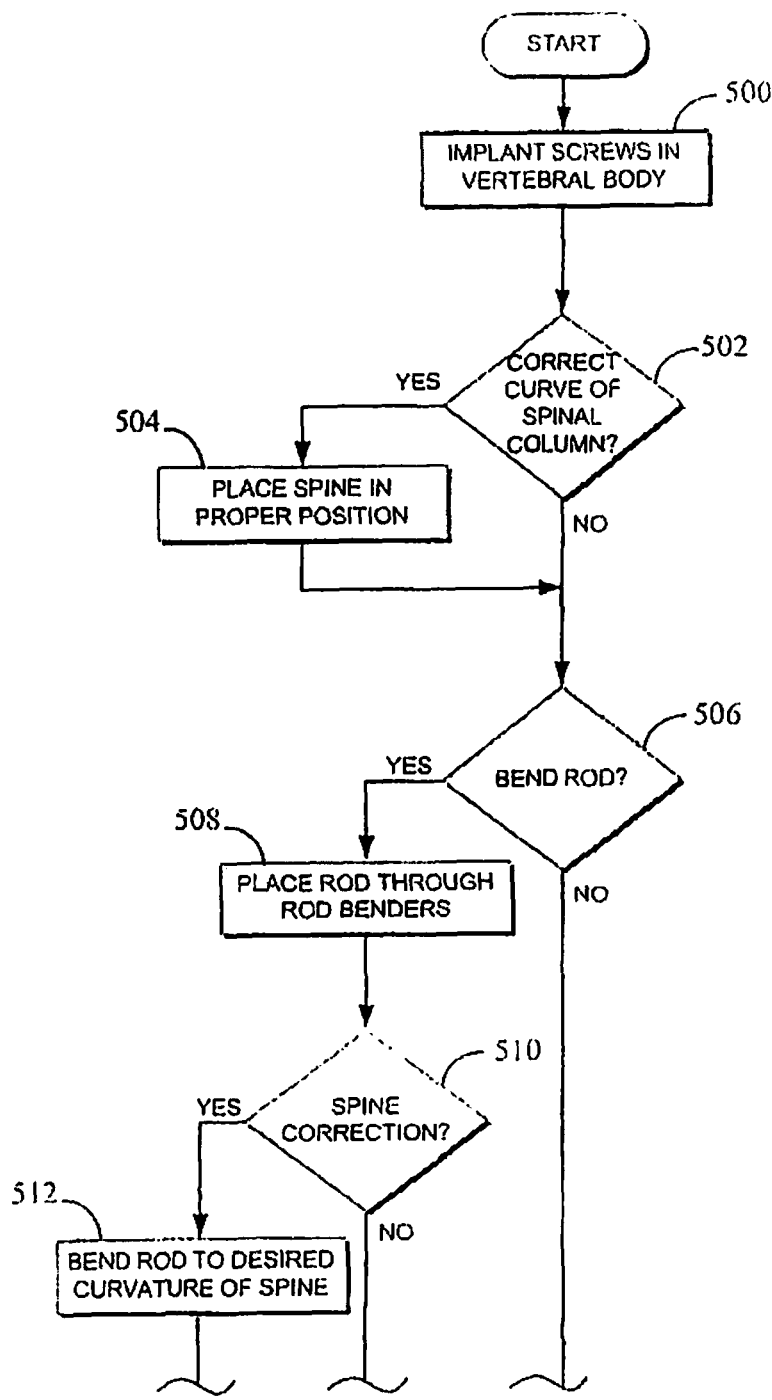
FIGS. 16A and 16B are flow charts illustrating an overview of a method of stabilizing a spine.
Figure 16B:
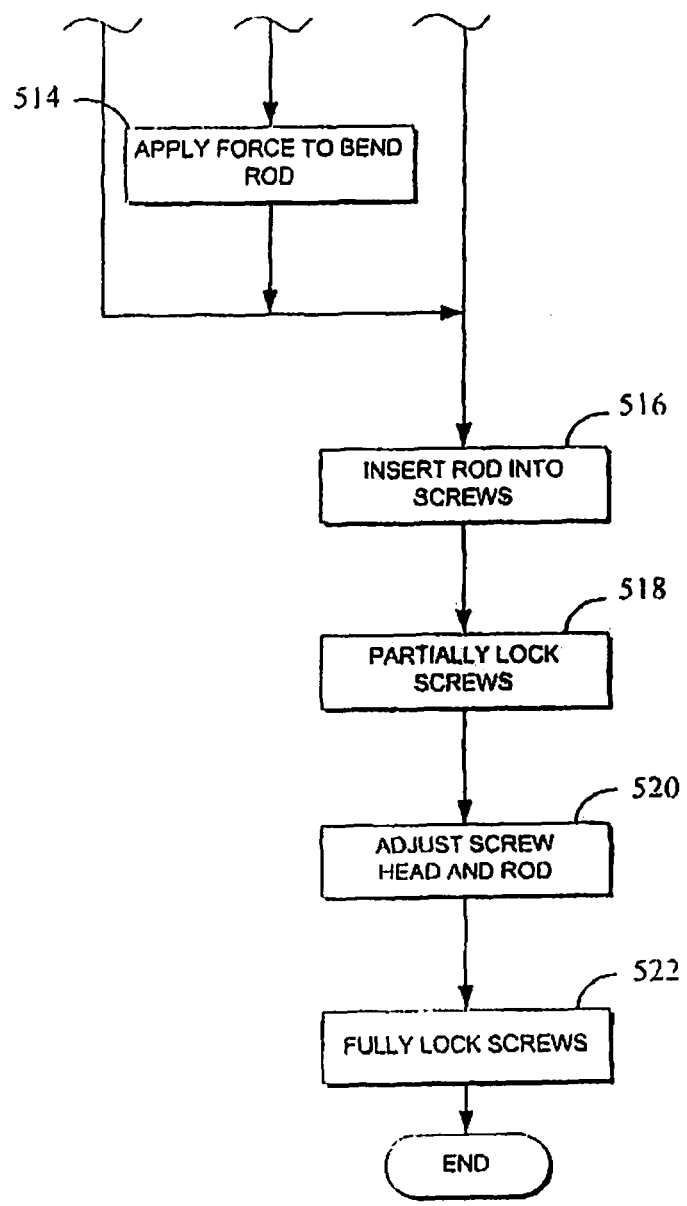

With reference now to FIGS. 16A and 16B, a method of performing spinal stabilization utilizing spinal stabilization system 100 is illustrated. Initially, the user implants a plurality of bone screws 50 in vertebral bodies of a patient in step 500. Preliminary to the operation of bone screw 50, outer housing 62 is positioned in the open/unlocked position, that is, outer housing 62 is moved downward relative to inner housing 64. Screw shaft 52 can then be driven into the desired vertebral body by providing torsional force via a driving tool (not shown) configured to mate with and grip bone screw 50. After screw shaft 52 is positioned within the vertebral body and the driving tool removed from the screw, elongate rounded section 12 of connecting rod 10 can be positioned transversely within connecting rod slot 70 defined in inner housing 64.

However, prior to securing connecting rod 10 with bone screw 50, the surgeon can manipulate and correct the curve of the spinal column, i.e., to manually manipulate and reduce the "rib hump" in step 502. After placing the spine in proper position in step 504, the surgeon can bend connecting rod 10 in step 506 prior to securing connecting rod 10 to the first two points of the spinal column where the construct is to be attached.

The surgeon can bend connecting rod 10 by utilizing the pair of rod bender devices 80 in step 508. In use, connecting rod 10 is inserted through selected apertures 88 of rod bender devices 80 and force is applied at handle members 82 of rod bender devices 80 to appropriately contour and shape connecting rod 10 to a desired curve in step 514.

In particular, spinal stabilization system 10 can be utilized to correct spinal deformity (see FIG. 15) in step 510 to appropriately contour and shape connecting rod 10 to a desired curvature of the spine, e.g., the sagittal curve, in step 512.

For example, a rod reduction device or plurality of rod reduction devices 150 including a screw jack mechanism and a manipulation device or plurality of manipulation devices 170 adapted and configured for attachment to heads of taper lock bone screws 50, and which provides leverage (i.e., long moment arm) to facilitate the manipulation of the spine may be utilized to orient the spine and place connecting rod 10 in bone screw 50. In particular, rod reduction device 150 includes a housing with two arms that are pivotally attached to the housing, an anvil movably mounted on the two arms, and a screw threadably coupled with the housing and the anvil. The distal ends of arms provide positive and secure attachment of rod reduction device 150 with bone screw 50. When the anvil is adjacent the housing the two arms are pivoted outwards, such that the distal ends of the arms can receive bone screw 50 therebetween. Rotating the screw of rod reduction device 150 in a first direction advances the screw through the housing and causes corresponding movement of the anvil toward bone screw 50, which in turn causes the arms to move toward each other and provides positive engagement with bone screw 50. The anvil defines an arcuately defined recess that is configured and dimensioned for positively engaging connecting rod 10. The recess cooperates with connecting rod slot 70 and defines an opening adapted for receiving connecting rod 10. With connecting rod 10 positioned in or near connecting rod slot 70, the surgeon continues to advance the screw capturing connecting rod 10 between the recess of the anvil and connecting rod slot 70. When the anvil is sufficiently advanced, the recess presses upon the outer surface of connecting rod 10 and pushes it into connecting rod slot 70. A suitable rod reduction device 150 is disclosed in a commonly assigned U.S. Patent Application Publication No. 2009/0018593, the complete disclosure of which is fully incorporated herein by reference.

Figure 15:
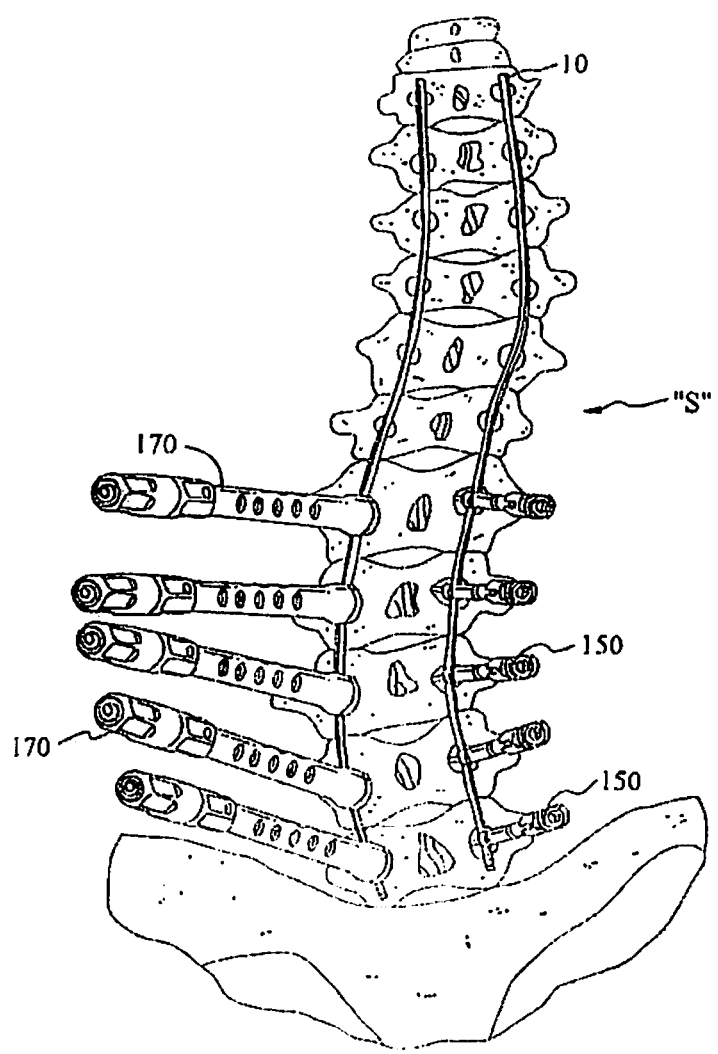
FIG. 15 is a perspective view of a spinal correction procedure on a deformed spine utilizing the spine stabilization system of FIG. 1.

With reference to FIG. 15, rod reduction device 150 is attached to the heads of bone screws 50 on the concave side of the spinal deformity. Manipulation device 170 is placed on bone screws 50 on the convex side of the spinal deformity. Depending on the nature of the deformity, however, rod reduction device 150 may be used on both sides of the deformity.

At this time, connecting rod 10 is positioned in slots 70 of bone screws 50 implanted in vertebral bodies in step 516. With screw shaft 52 and screw head 54 being fixed in position relative to the vertebral body, bone screws 50 may be partially locked in step 518. In particular, inner housing 64 and the circumferentially disposed outer housing 62 can be articulated relative to screw head 54 as necessary to manipulate the disposition of connecting rod 10 within bone screw 50 to make necessary adjustments in step 520. For example, bone screw 50 may be partially locked to connecting rod 10 for compression, distraction and rotation without torsional stress being applied to the spine.

Upon completion of the necessary positional adjustments of inner housing recess 66 relative to screw head 54 and the adjustments of connecting rod 10 relative to connecting rod slot 70, outer housing 62 can be grasped by the operator using the complementarily configured locking device. Activation of the locking device slides the outer housing upward circumferentially over the outer surface of inner housing 64 while the push rod holds down connecting rod 10 and inner housing 64 so that bone screw 50 is reconfigured from the open or unlocked position to closed or locked position in step 522. Similarly, the operator can use the complementarily configured unlocking device to grasp inner housing 64 and slidably move outer housing 62 downward along the outer surface of inner housing 64 from a closed or locked position to an open or unlocked position. The rod and bone screw combination of the present disclosure may provide particular advantages in scoliosis or other spinal deformity surgery in which high stress levels are exerted upon such constructs at particular levels in the construct or over the entire length of such a construct.

Figure 17:
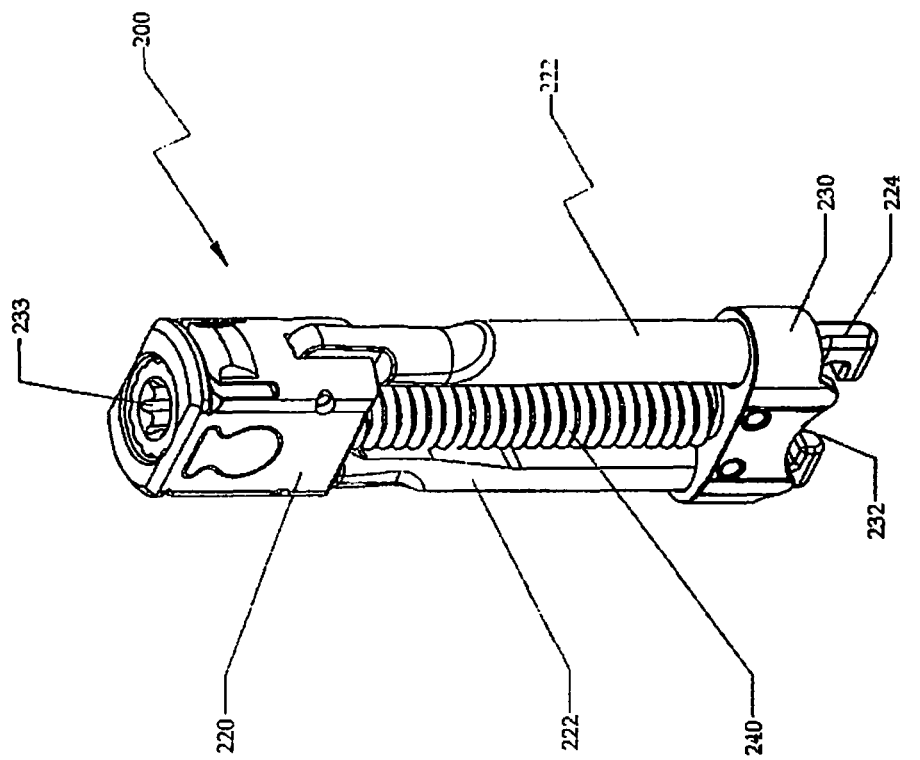
FIG. 17 is a perspective view of a rod reduction device for use with the spinal stabilization system of FIG. 1.
Figure 17A:
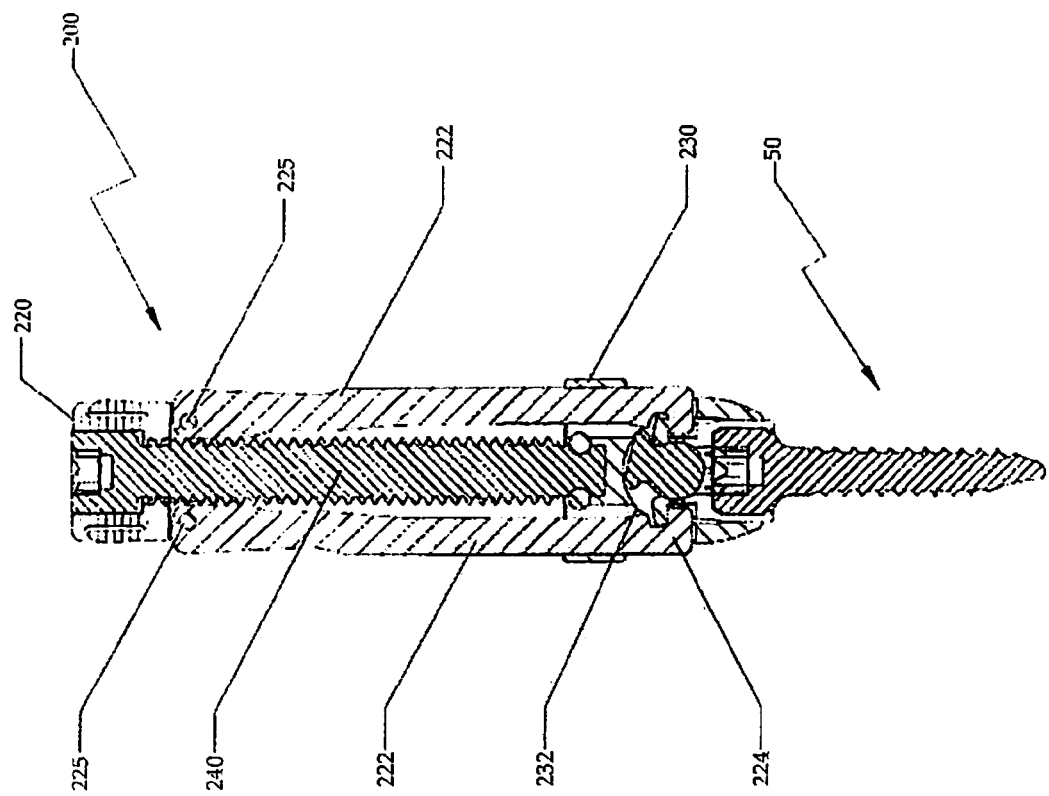
FIG. 17A is a front, cross-sectional view of the rod reduction device of FIG. 17 operatively connected to a screw and a connecting rod.

With reference to FIGS. 17 and 17A, spinal stabilization system 100 may further include a rod reduction device 200 configured and adapted for attachment to housing 60 of taper lock bone screws 50. In particular, rod reduction device 200 includes a housing 220 with two arms 222 that are pivotally attached to housing 220, an anvil 230 movably mounted on two arms 222, and a screw 240 threadably coupled with housing 220 and anvil 230. In particular, each arm 222 pivots about a pivot pin 225 disposed in housing 220, whereby each arm 222 pivots relative to housing 220. Distal ends 224 of arms 222 provide positive and secure attachment of rod reduction device 200 with bone screw 50. When anvil 230 is adjacent housing 220, two arms 222 are pivoted outwards, such that distal ends 224 of arms 222 can receive bone screw 50 therebetween. Screw 240 may be rotated using a tool (not shown) that engages a recess 233 in screw 240. Rotating screw 240 of rod reduction device 200 in a first direction advances screw 240 through housing 220 and causes corresponding movement of anvil 230 toward bone screw 50, which in turn causes arms 222 to move toward each other and provides positive engagement with bone screw 50.

Anvil 230 has an arcuately defined recess 232 that is configured and dimensioned for positively engaging connecting rod 10. The arcuate shape of recess 232 accommodates, i.e., drives, connecting rod 10 into bone screw 50, independent of the orientation of connecting rod 10. Recess 232 cooperates with connecting rod slot 70 and defines an opening adapted for receiving connecting rod 10. With connecting rod 10 positioned in or near connecting rod slot 70, the surgeon continues to advance screw 240 capturing connecting rod 10 between recess 232 of anvil 230 and connecting rod slot 70. When anvil 230 is sufficiently advanced, recess 232 presses upon the outer surface of connecting rod 10 and urges it into connecting rod slot 70.

With reference to FIGS. 18-18B, spinal stabilization system 100 may also include a partial locker 300. Partial locker 300 includes a distal end portion 310 configured to be received about reduction device 200 while reduction device 200 remains operably engaged with inner housing 64 of bone screw 50. In particular, distal end portion 310 of partial locker 300 includes a plurality of graspers 322 configured to engage outer housing 62 of bone screw 50. In particular, the plurality of graspers 322 are coupled operatively with a handle member 350. When handle member 350 is in an unactuated position, as shown in FIG. 18, the plurality of graspers 322 extend radially outward, and when handle member 350 is in an actuated position, as shown in FIGS. 18A and 18B, the plurality of graspers 322 move radially inward to engage outer housing 62 and to move outer housing 62 relative to inner housing 64 to partially lock connecting rod 10 to dual layered housing 60. A suitable partial locker is disclosed in commonly assigned U.S. Patent Application Publication Nos. 2009-0018593 and 2007-0093817, the complete disclosures of which are fully incorporated herein by reference.

With reference now to FIGS. 19-19B, spinal stabilization system 100 may further include a quick locker 500 including a distal end portion 510 that is configured to operably engage outer housing 62 of bone screw 50 and connecting rod 10. In particular, quick locker 500 is used after reduction device 200 has been disengaged from dual layered housing 60 of bone screw 50. Distal end portion 510 is configured to move outer housing 62 with respect to connecting rod 10 to fully lock connecting rod 10 to dual layered housing 60. Optionally, connecting rod 10 may be partially locked with dual layered housing 60.

Figure 20:
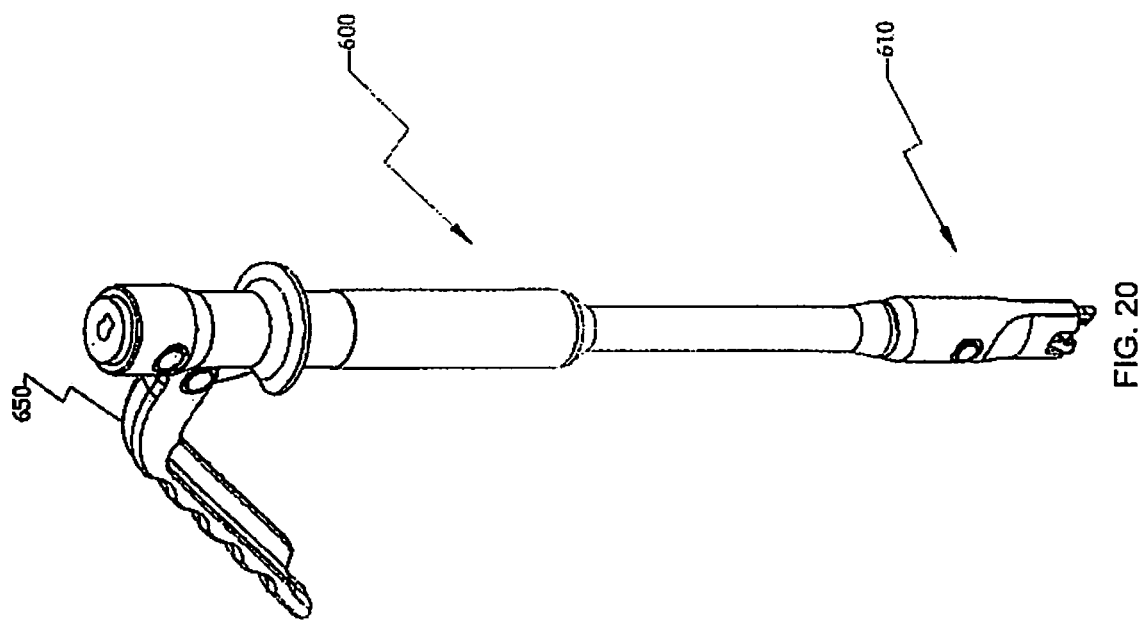
FIG. 20 is a perspective view of an unlocker for use with the spinal stabilization system of FIG. 1.
Figure 21:
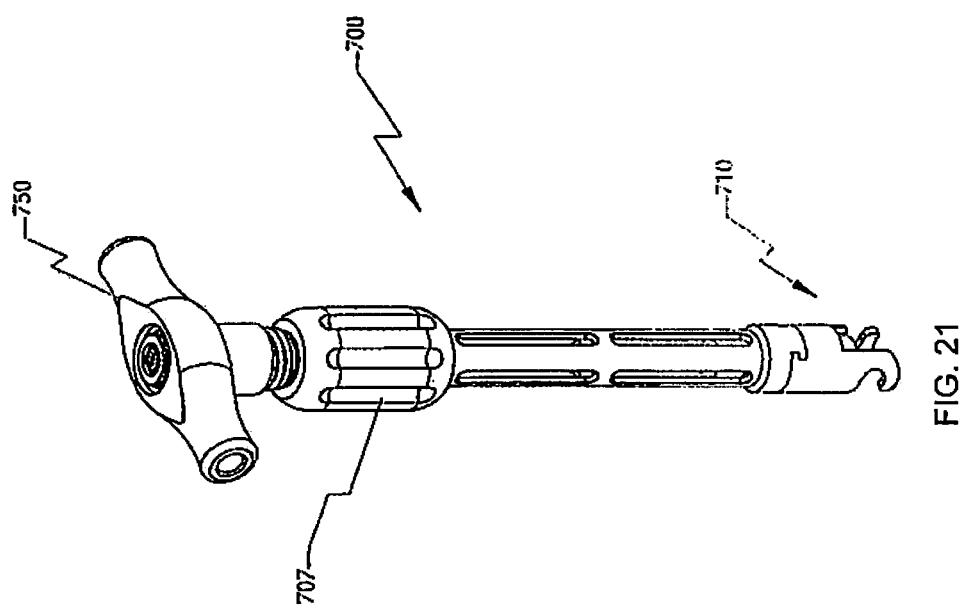
FIG. 21 is a perspective view of a rod puller for use with the spinal stabilization system of FIG. 1.

With reference now to FIGS. 20-21A, an unlocker 600 and a rod puller 700 may also be provided as part of spinal stabilization system 100. Unlocker 600 includes a distal end portion 610 having a pair of arm members 622 coupled operatively to a lever 650. Each arm member 622 includes a grasper 622a. The pair of graspers 622a are configured and adapted to engage outer housing 62 of bone screw 50 to move outer housing 62 relative to inner housing 64 and connecting rod 10 to fully unlock connecting rod 10 from dual layered housing 60. In particular, when lever 650 is squeezed against an elongate body 630, graspers 622a move outer housing 62 distally relative to inner housing 64 and connecting rod 10 to fully unlock connecting rod 10 from dual layered housing 60. Upon fully unlocking connecting rod 10 from dual layered housing 60, rod puller 700 may be utilized to remove connecting rod 10 from connecting rod slot 70 of inner housing 64 of bone screw 50. Rod puller 700 includes a distal end portion 710 having a pair of spaced apart hook portions 722 configured and adapted to engage connecting rod 10. In particular, hook portion 722 is coupled operatively with a rotating handle 750 to enable concomitant rotation therewith. Rotating handle 750 may be rotated to facilitate alignment of hook portion 722 with connecting rod 10, as well as facilitating disengagement of rod 10 from connecting rod slot 70. In this manner, the clinician may perform the unseating of connecting rod 10 from within connecting rod slot 70 of inner housing 64 of bone screw 50 through pulling of a handle member 707 when connecting rod 10 is engaged with hook portion 722, as well as rotating rotating handle 750.

Figure 23:
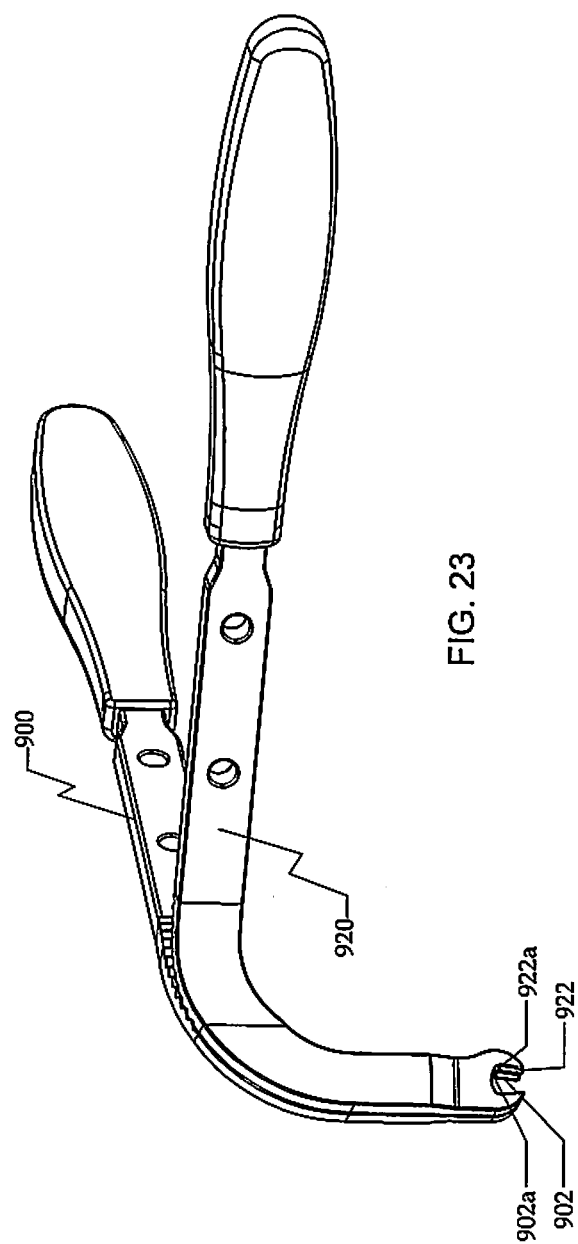
Figure 24:
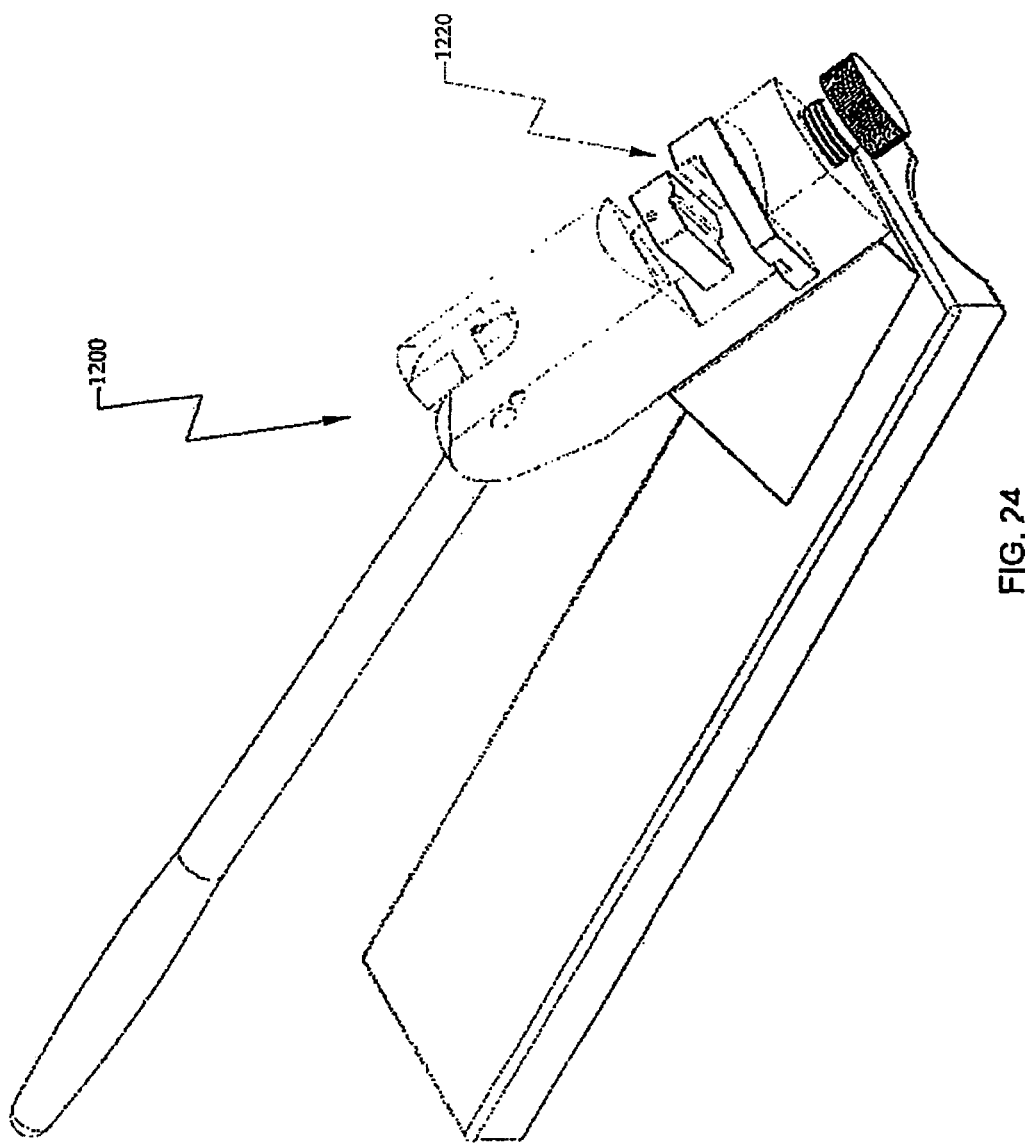

With reference to FIGS. 22-24, spinal stabilization system 100 may further include right and left in situ rod benders 800, 820, right and left coronal rod benders 900, 920 and a tabletop rod bender 1200. Right and left in situ rod benders 800, 820 each define a slot 802, 822, respectively, for selective reception of connecting rod 10 therein. In particular, each slot 802, 822 has a substantially rectangular wall 802a, 822a configured to engage elongate head portion 14 of connecting rod 10 in a single orientation. Right and left in situ rod benders 800, 820 are configured for bending connecting rod 10 subsequent to placement of connecting rod 10 within the body. Right and left coronal rod benders 900, 920 also each define a slot 902, 922, respectively, for selective reception of connecting rod 10 therein. Each slot 902, 922 includes an arcuate end wall 902a, 922a configured to engage elongate rounded section 12 of connecting rod 10 in a single orientation. Right and left coronal rod benders 900, 920 are configured for bending connecting rod 10 prior to placement of connecting rod 10 within the body. Table top bender 1200 includes a jaw mechanism 1220 configured and adapted for bending connecting rod 10. Table top bender 1200 includes an alternative jaw mechanism (not shown) configured for cutting connecting rod 10.

With reference to FIGS. 25-31, spinal stabilization system 100 may further include a cross connector assembly 1000 configured to couple connecting rods 10 to each other. Cross connector assembly 1000 includes a pair of connectors 1020 and an intermediate portion 1050 connecting the pair of connectors 1020. Each connector 1020 defines a recessed portion 1022 configured to be fixed securely to connecting rod 10. In particular, each connector 1020 defines a slit 1024 configured to flex or enlarge the dimensions of recessed portion 1022 to facilitate insertion of connecting rod 10. Recessed portion 1022 includes a substantially rectangular wall 1022a configured to engage elongate head portion 14 of connecting rod 10 and an opposing arcuate wall 1022b configured to engage elongate rounded section 12 of connecting rod 10. In particular, recessed portion 1022 includes fingers 1022c to secure connecting rod 10 within recess portion 1022.

In addition, each connector 1020 defines a bore 1026 (FIG. 29) and a socket 1028 (FIG. 29). Bore 1026 is configured and dimensioned to receive a screw 1044. Socket 1028 is configured and dimensioned to receive a ball joint 1052, 1054 of intermediate portion 1050. Each connector 1020 further defines a slit 1032 configured to flex or enlarge socket 1028 to facilitate insertion of ball joint 1052, 1054 of intermediate portion 1050 therein.

Upon insertion of connecting rod 10 in recessed portion 1022 and ball joint 1052, 1054 in socket 1028, screws 1044 are inserted into a respective bore 1026 to fix connecting rod 10 and ball joint 1052 in recessed portion 1022 and socket 1028, respectively.

With particular reference now to FIG. 29, intermediate portion 1050 includes an insertion arm 1060 and a receiving arm 1070. Receiving arm 1070 defines a recessed portion 1072 configured and dimensioned to receive slidably insertion arm 1060 therein. Insertion arm 1060 defines a bore 1066 configured to receive a set screw 1033 to fix a relative position of arms 1060, 1070. In this manner, the length of intermediate portion 1060 may be adjustable by the clinician. Insertion arm 1060 and receiving arm 1070 include ball joint 1054, 1052 configured to be received in socket 1028. Under such a configuration, ball joints 1052, 1554 enable variable or polyaxial adjustment between connector 1020 and intermediate portion 1050 prior to fastening of screw 1044. As such, the length and orientation of intermediate portion 1050 relative to connector 1020 may be selectively chosen by the clinician prior to fastening set screw 1033 and screws 1044.

With reference to FIG. 32, spinal stabilization system 100 may further include a cross connector assembly 2000 configured to couple various connecting rods 10, 11 to each other. For example, connecting rod 11 is a 5.5 mm diameter round rod. Connecting rod 10, as described hereinabove, includes elongate rounded section 12 having a substantially circular cross-section, an elongate head portion 14, and a neck portion 16 that connects and transitions elongate rounded section 12 into elongate head portion 14, and thereby providing reduced stress concentration along the elongate body of connecting rod 10.

Cross connector assembly 2000 includes connectors 2020, 2030. Connector 2020 defines a recessed portion 2022 configured to receive connecting rod 11 therein. Similar to connector 1020, connector 2020 defines a slit 2024 configured to flex or enlarge the dimensions of recessed portion 2022 to facilitate insertion of connecting rod 11. Recessed portion 2022 includes a pair of opposing fingers 2022a (only one shown) to secure connecting rod 10 within recess portion 2022. In addition, connector 2020 defines a bore 2026 and a socket 2028. Bore 2026 is configured and dimensioned to receive a screw 1044. Socket 2028 is configured and dimensioned to receive a ball joint 2052 of connector 2030. Connector 2020 further defines a slit 2032 configured to flex or enlarge socket 2028 to facilitate insertion of ball joint 2052 of connector 2030.

Connector 2030 includes an elongate body 2035 having ball joint 2052 configured and dimensioned to be received in socket 2028 and a grasping portion 2070. In particular, grasping portion 2070 defines a recess 2071 configured and dimensioned to receive at least a portion of elongate head portion 14 of connecting rod 10. Recess 2071 has a substantially rectangular shape configured to engage elongate head portion 14 of connecting rod 10. Moreover, recess 2071 defines a pair of opposing fingers 2071a that secures elongate head portion 14 within recess 2071. In order to secure elongate head portion 14 between opposing fingers 2071a, connector 2030 may be made of a material that provides suitable flexibility to provide a snap-fit engagement with elongate head portion 14. Alternatively, connector 2030 may be made of a rigid material in which case, one end of elongate head portion 14 may slide into recess 2071.

In addition, connector 2030 further defines a bore 2075 configured and dimensioned to receive screw 1044 to fix connecting rod 10 to connector 2030. Upon insertion of connecting rod 11 in recessed portion 2022 and ball joint 2052 of connector 2030 in socket 2028 of connector 2020, screw 1044 is inserted into bore 2026 to fix connecting rod 11 in recessed portion 2022 and ball joint 2052 in socket 2028. Similarly, screw 1044 is used to secure connecting rod 10 with connector 2030. In this manner, cross connector assembly 2000 enables coupling of various connecting rods with various cross-sections and diameters.

With reference now to FIG. 33, spinal stabilization system 100 may further include a cross connector assembly 3000 configured to couple connecting rods 10 to each other. Cross connector assembly 3000 includes an elongate body 3035 having a grasping portion 3070 at one end of elongate body 3035 and a grasping portion 3090 at another end of elongate body 3035. The structure and method of using grasping portions 3070, 3090 are substantially identical to grasping portion 2070, as described hereinabove, and thus will not be described herein.

With reference now to FIGS. 34 and 34A, spinal stabilization system 100 may further include an axial connector 4000. Axial connector 4000 is configured to connect connecting rods 10, 11 in a substantially linear fashion. However, the type of rods axial connector 4000 may connect are not limited to connecting rods 10, 11. Axial connector 4000 may be used to extend a rod construct that exists on the same side of the spinous process or to change rod diameter or type along the construct. Due to the deformity being corrected, it is sometimes beneficial to have different rod types to allow for a change in the type of correction needed. The axial connector 4000 is locked to the connecting rods 10, 11 with screws 1044.

With continued reference to FIGS. 34 and 34A, axial connector 4000 includes an elongate body 4100 defining a longitudinal bore 4102. The cross-section of longitudinal bore 4102 generally corresponds to the cross-section of connecting rod 10. In this manner, both connecting rods 10, 11 can be received through longitudinal bore 4102. Moreover, elongate body 4100 further defines a plurality of bores 4045 configured and dimensioned to receive screws 1044 therein to fix connecting rods 10, 11 to axial connector 4000. As described above, it is contemplated that various connecting rods may be used with axial connector 4000. For example, two connecting rods 10 may be used for a suitable construct, as shown in FIG. 35.

Figure 36:
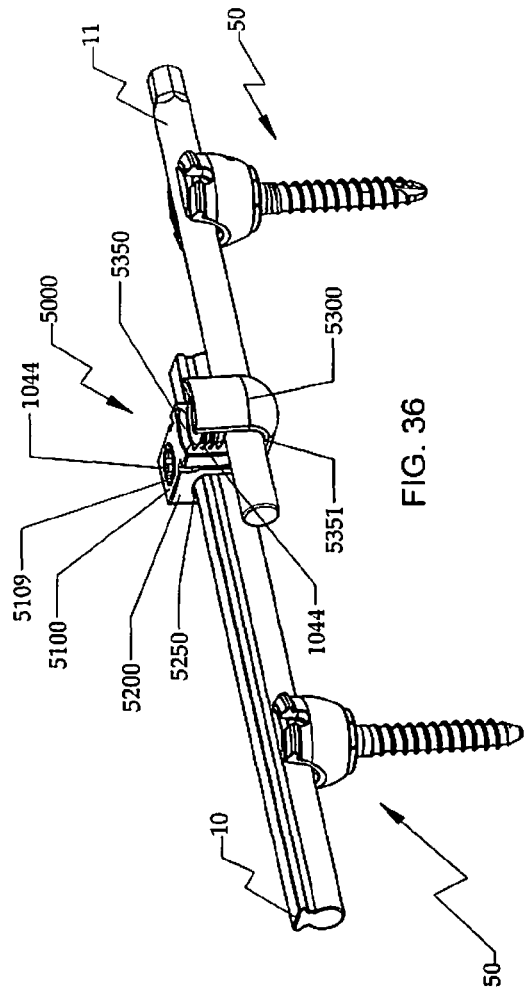
FIG. 36 is a perspective view of an offset connector illustrating use with different connecting rods.
Figure 36:
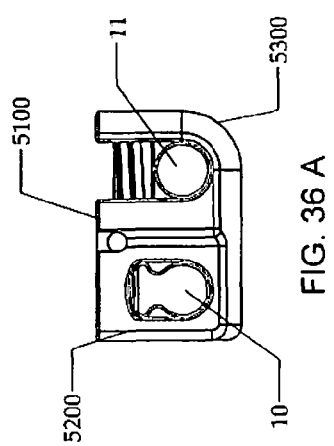

With reference now to FIGS. 36 and 36A, spinal stabilization system 100 may further include an offset connector 5000 to connect, for example, connecting rods 10, 11. Offset connector 5000 may typically be used to extend a rod construct that exists on the same side of the spinuous process or to change rod diameter or type along the construct. Due to the deformity being corrected, it is sometimes beneficial to have different rod types to allow for a change in the type of correction needed. Offset connector 5000 is locked to connecting rods 10, 11 with set screws.

Figure 37:
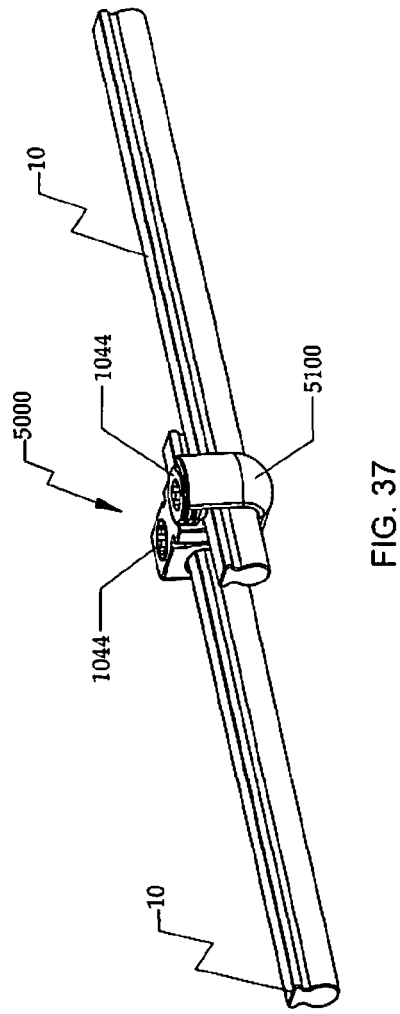
FIG. 37 is a perspective view of the offset connector of FIG. 36 illustrating use with the connecting rods of FIG. 1.
Figure 37:
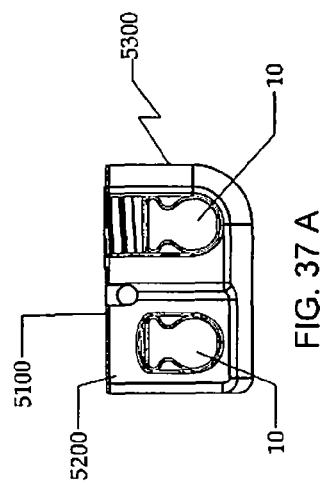

With continued reference to FIGS. 36 and 36A, offset connector 5000 includes a body 5100. Body 5100 includes a first connecting portion 5200 and a second connecting portion 5300 disposed adjacent first connecting portion 5200. First connecting portion 5200 defines a bore 5250 configured and dimensioned to receive connecting rod 10 therethrough. First connecting portion 5200 further defines a hole 5109 to threadably receive screw 1044 to fix connecting rod 10 with first connecting portion 5200. Second connecting portion 5300 defines a recess 5350 configured and dimensioned to receive connecting rod 11. Recess 5350 may define an arcuate portion 5351 to accommodate connecting rods with circular cross-section. Preferably, recess 5350 has a depth greater than the diameter of connecting rod 11, such that various diameter connecting rods may be accommodated in recess 5350. The varying diameter of various connecting rods will be fixed securely in second connecting portion 5300 by screw 1044. In addition, offset connector 5000 is not limited to the combination of connecting rods 10, 11. For example, a pair of connecting rods 10 may be used with offset connector 5000, as shown in FIGS. 37 and 37A.

Figure 38:
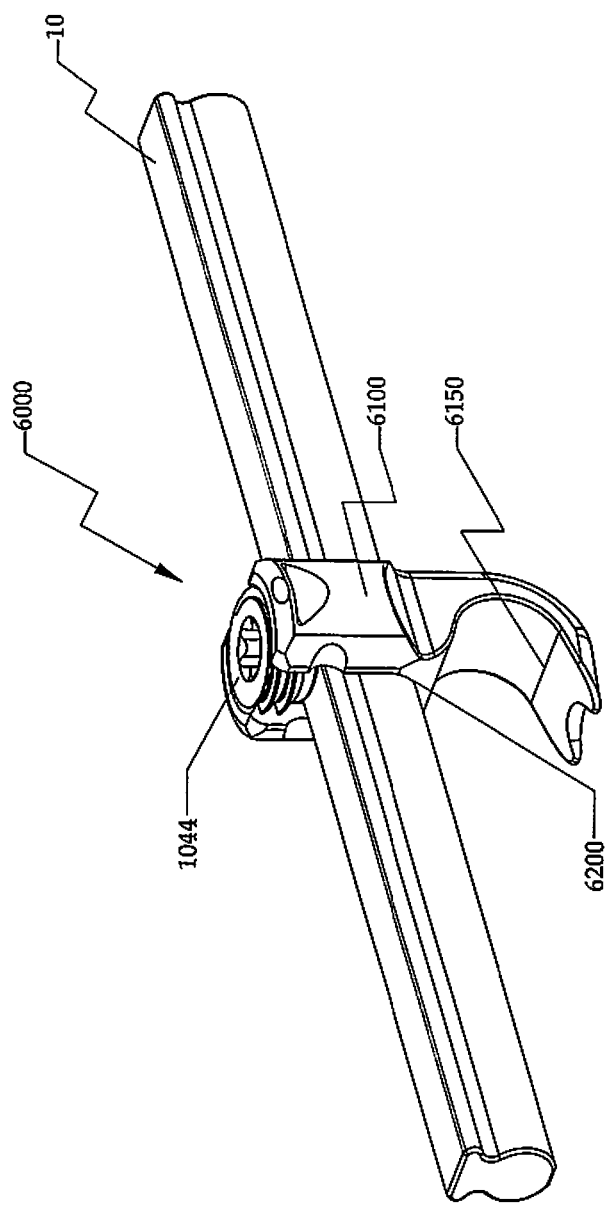
FIG. 38 is a perspective view of a spinal hook for use with the spinal stabilization system of FIG. 1.
Figure 38:
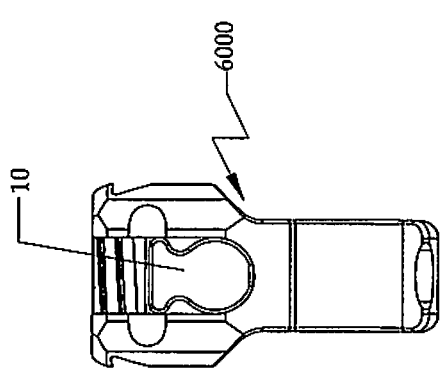

With reference now to FIGS. 38 and 38A, spinal stabilization system 100 may further include a spinal hook 6000. Spinal hook 6000 may be used to connect the connecting rod to the anatomy in various locations. Some spinal hooks 6000 are used with the lamina, others with the pedicle. Spinal hook 6000 can also have a variety of sizes, shapes and angles to accommodate the anatomy. The spinal hook 6000 may be locked to connecting rod 10 with screw 1044. Spinal hook 6000 includes a body 6100 and a hook 6150 extending therefrom. Body 6150 defines a recess 6200 configured and dimensioned to receive connecting rod 10 therein. The cross-section of recess 6200 generally corresponds to the cross-section of connecting rod 10, which also accommodates round connecting rod 11. As described above, it is contemplated that various connecting rods may be used with spinal hook 6000. Screw 1044 is used to fix connecting rod 10 to spinal hook 6000.

In use, two or more bone screws 50 are affixed to two or more vertebral bodies. Connecting rod 10 is then bent using one or more of the rod benders 80, 800, 820, 900, 920, 1200 to conform connecting rod 10 to the configuration necessary to achieve proper alignment of the vertebral bodies. Once connecting rod 10 is appropriately bent, a clinician places connecting rod 10, by hand, in alignment with dual layered housing 60 of bone screws 50 such that elongate rounded portion 12 is received within connecting rod slot 70 of dual layered housing 60 of bone screw 50. Once connecting rod 10 is properly aligned with dual layered housing 60 of bone screw 50, reduction device 200 is attached to dual layered housing 60 to seat connecting rod 10 within connecting rod slot 70 of bone screw 50. Partial locker 300 is then placed over reduction device 200 and engaged with dual layered housing 60 of bone screw 50 to partially lock connecting rod 10 to dual layered housing 60. Partial locker 300 and one or more reduction devices 200 are then disengaged from dual layered housing 60. At this point, connecting rod 10 may be rotationally adjusted relative to dual layered housing 60 of bone screw 50. In situ benders 800, 820 may also be used to further bend connecting rod 10. Upon proper orientation of connecting rod 10, quick locker 500 is engaged with dual layered housing 60 of bone screw 50 to fully lock connecting rod 10 within dual layered housing 60 of bone screw 50.

In the case of using more than one connecting rod 10, 11, cross connectors 1000, 2000, 3000, axial connector 4000, and/or offset connector 5000 may be utilized to further secure connecting rods 10, 11 to vertebrae. Initially, a bone screw 50 is inserted into a pedicle and another is inserted into a pedicle of the same vertebral level on the opposite side of the spinous process. Two additional bone screws 50 are inserted into pedicles at a position cranial (or distal) to the first two screws 50 at the same vertebral level. A connecting rod 10, 11 is inserted into two bone screws on one side of the spinous process and another connecting rod (of the same or different cross section or diameter) 10, 11 is inserted into the two bone screws 50 on the opposite side of the spinous process. Bone screws 50 are locked and then a suitable cross connector 100, 2000, 3000 is attached to the two connecting rods 10, 11 and locked into place. Spinal hook 6000 may be used as needed to provide additional stabilization.

Another method involves the construct above and in addition, the placement of axial connector 4000 at the distal end of both connecting rods 10, 11. Subsequent to the placement of axial connector 4000, two more bone screws 50 are inserted into opposing pedicles at the same or different vertebral level. A connecting rod 10, 11 (of the same or different diameter or cross section) is inserted into bone screws 50 and into axial connectors 4000. Bone screws 50 are locked to connecting rods 10, 11 and axial connectors 4000 are locked to connecting rods 10, 11 to complete the construct. Alternatively, offset connector 5000 may be used.

With reference to FIGS. 39 and 40, another embodiment of the present disclosure is shown generally as a spinal stabilization system 1000. Spinal stabilization system 1000 includes at least one bone screw 50 and a connecting rod 500 releasably secured to bone screw 50. Connecting rod 500 is configured and dimensioned to be selectively and releasably secured to bone screw 50. Connecting rod 500 is defined by an elongate body of a particular length. The elongate body is made of a biocompatible material such as Titanium (Ti-CP) and its alloys (e.g., Ti-6Al-4V), Cobalt-Chrome Alloy (CoCr) or Stainless Steel (SS).

With particular reference to FIG. 39, the elongate body of connecting rod 500 includes a first portion 510, a second portion 570, and a transition portion 550 that connects or transitions first portion 510 to second portion 570. First portion 550 is substantially identical to connecting rod 10. First portion 550 includes an elongate rounded section 512 having a substantially circular cross-section, an elongate head portion 514, and a neck portion 516 that connects and transitions elongate rounded section 512 into elongate head portion 514, and thereby providing reduced stress concentration along the elongate body of first portion 510.

Elongate rounded section 512 of first portion 510 is configured and dimensioned to be received in connecting rod slot 70 of inner housing 64. For example, rounded section 512 of first portion 510 may have a standard diameter of, for example, about 5.5 mm, suitable to mate with connecting rod slot 70.

Elongate head portion 514 has a substantially rectangular cross-section having suitable dimensions of, for example, about 6 mm×about 1 mm (0.246 in.×0.039 in.). However, it is envisioned that elongate head portion 514 may have a cross-section that is substantially square, elliptical or any other shape to add rigidity to rounded section 512 of first portion 510.

Neck portion 516 has dimensions that are smaller than those of elongate rounded section 512 and elongate head portion 514. Neck portion 516 defines a pair of concave sides joining elongate head portion 514 to elongate rounded section 512, so that the concave sides provide clearance for the taper lock screw housings.

Bone screw 50 may be positioned at any desired position along the elongate body of connecting rod 500. When first portion 510 is secured to bone screw 50, neck portion 516 of first portion 510 is disposed at the top of bone screw 50 and does not interfere with the interaction between first portion 510 and bone screw 50. Furthermore, elongate head portion 514 of first portion 510 is disposed above the top of taper lock screw 50.

With continued reference to FIG. 39, transition portion 550 transitions first portion 510 to second portion 570. Transition portion 550 is configured to reduced stress concentration along the elongate body of connecting rod 500. In particular, transition portion 550 includes an elongate head portion 554, an elongate rounded section 552 that is substantially identical to elongate rounded section 512 of first portion 510, and a neck portion 556 that connects and transitions elongate rounded section 552 into elongate head portion 554. In particular, transition portion 550 is longitudinally tapered such that an end portion thereof adjacent first portion 510 has a cross section that is substantially identical to a cross section of first portion 510 and an opposite end portion thereof adjacent second portion 570 has a cross section that is substantially identical to a cross section of second portion 570. Second portion 570 includes a circular rod 600 concentrically aligned and coupled to elongate rounded section 552 of transition portion 550. Circular rod 600 is configured and dimensioned to be received in connecting rod slot 70 of bone screw 50.

First portion 510 provides a greater stiffness and rigidity than circular rod 600 of second portion 570. Under such a configuration, a single body connecting rod 500 provides a non-uniform stiffness and rigidity. In addition, first and second portions 510, 570 do not require any design changes to taper lock screw 50, and thus advantageously provide efficiency of manufacture and inventory. The elongate body of connecting rod 500 may be monolithically formed as a unitary construct. For example, connecting rod 500 may be machined from a single piece of bar stock.

Although the illustrative embodiments of the present disclosure have been described herein with reference to the accompanying drawings, the above description, disclosure, and figures should not be construed as limiting, but merely as exemplifications of particular embodiments. For example, it is contemplated that elongate head portion 14 of connecting rod 10 need not extend over substantially the entire the elongate body of connecting rod 10, but instead may only be provided in a portion of connecting rod 10 where it is desired to enhance the rigidity of that portion of the rod. One skilled in the art will recognize that the present disclosure is not limited to use in spine surgery, and that the instrument and methods can be adapted for use with any suitable surgical device. It is to be understood, therefore, that the disclosure is not limited to those precise embodiments, and that various other changes and modifications may be effected therein by one skilled in the art without departing from the scope or spirit of the disclosure.

What is claimed is:

1. A spinal stabilization system comprising:
a connecting rod including an elongate round portion, an elongate head portion including a planar surface, and a neck portion connecting the elongate round portion with the elongate head portion; and
a bone screw including a housing portion and a screw shaft extending distally from the housing portion, the housing portion including an inner housing and an outer housing slidably surrounding at least a portion of the inner housing, the inner housing defining a slot configured and dimensioned to releasably secure the elongate round portion of the connecting rod therein, wherein the outer housing is movable relative to the inner housing between an unlocked state in which the elongate round portion of the connecting rod is releasable from the slot defined in the inner housing and a locked state in which the connecting rod is secured in the slot, wherein a cross-section of the connecting rod is asymmetric about an axis of the connecting rod, and the elongate head portion extends away from the inner housing when the elongate round portion is disposed in the slot of the inner housing.

2. The spinal stabilization system according to claim 1, wherein the elongate head portion of the connecting rod has a non-circular cross-section.

3. The spinal stabilization system according to claim 1, wherein the elongate head portion of the connecting rod has a substantially rectangular cross-section.

4. The spinal stabilization system according to claim 1, wherein the neck portion of the connecting rod has an arcuate profile.

5. The spinal stabilization system according to claim 4, wherein the neck portion is narrower than the elongate round portion.

6. The spinal stabilization system according to claim 1, wherein the connecting rod is monolithically formed.

7. The spinal stabilization system according to claim 1, wherein the screw shaft is polyaxially coupled to the housing portion.

8. The spinal stabilization system according to claim 1, wherein the outer housing includes a circumferentially disposed flange.

9. The spinal stabilization system of claim 1, further comprising a plurality of bone screws.

10. The spinal stabilization system according to claim 1, wherein the axis of the connecting rod extends through the neck portion.

11. The spinal stabilization system according to claim 10, wherein the neck portion includes concave sides.

12. A spinal stabilization system comprising:
a bone screw including a housing defining a slot; and
a connecting rod including:
an elongate round section configured to be received in the slot of the bone screw;
an elongate head portion; and a neck portion connecting the elongate round section to the elongate head portion, wherein the neck portion and the elongate head portion extend away from the housing when the elongate round section is disposed in the slot, wherein a cross-section of the connecting rod is asymmetric about an axis of the connecting rod, wherein the elongate head portion, the elongate round section, and the neck portion are formed as a unitary construct.

13. The spinal stabilization system according to claim 12, wherein the housing includes an inner housing and an outer housing selectively positionable relative to the inner housing to lock the connecting rod in position within the slot defined by the inner housing.

14. The spinal stabilization system according to claim 13, wherein the outer housing is transitionable relative to the inner housing between a locked position in which the connecting rod is fully locked in position within the inner housing and an unlocked position in which the connecting rod is movable within the inner housing, wherein the neck portion is configured to provide a space to permit transition of the outer housing between the locked and unlocked positions.

15. The spinal stabilization system according to claim 13, wherein the neck portion is spaced apart from the inner housing when the elongate round section is disposed in the slot.

16. The spinal stabilization system according to claim 12, wherein the elongate head portion has a non-circular cross-section.

17. The spinal stabilization system according to claim 12, wherein the neck portion of the connecting rod has an arcuate profile.

18. The spinal stabilization system according to claim 12, wherein the neck portion defines a pair of concave sides joining the elongate head portion to the elongate round section.

19. The spinal stabilization system according to claim 12, wherein the elongate round section has a generally circular cross-section.

20. The spinal stabilization system according to claim 12, wherein the neck portion is narrower than the elongate round section.

21. The spinal stabilization system according to claim 12, wherein the elongate head portion, the elongate round section, and the neck portion are monolithically formed.

22. The spinal stabilization system according to claim 12, wherein at least one of the elongate round section, the elongate head portion, or the neck portion is formed from a biocompatible material.

23. The spinal stabilization system according to claim 12, wherein at least one of the elongate round section, the elongate head portion, or the neck portion is formed from a material selected from a group consisting of titanium, titanium alloy, cobalt-chrome alloy, and stainless steel.

24. The spinal stabilization system according to claim 12, wherein the elongate head portion has a substantially rectangular cross-section.

25. A spinal stabilization system comprising:
a connecting rod including a first portion and a second portion, the first portion including an elongate round portion, an elongate head portion including a planar surface, and a neck portion connecting the elongate round portion with the elongate head portion, the second portion including a circular rod, the circular rod coupled to the elongate round portion; and
a bone screw including a housing portion and a screw shaft extending distally from the housing portion, the housing portion including an inner housing and an outer housing slidably surrounding at least a portion of the inner housing, the inner housing defining a slot configured and dimensioned to releasably secure the connecting rod therein, wherein the outer housing is movable relative to the inner housing between an unlocked state in which the connecting rod is releasable from the slot defined in the inner housing and a locked state in which connecting rod is secured to the slot, wherein a cross-section of the first portion of the connecting rod is asymmetric about an axis of the first portion, and the elongate head portion extends away from the inner housing when the elongate round portion is disposed in the slot of the inner housing.

26. The spinal stabilization system according to claim 25, wherein the connecting rod further includes a transition portion connecting the first and second portions, the transition portion being longitudinally tapered.

27. The spinal stabilization system according to claim 26, wherein the transition portion includes a first end having a cross section substantially identical to a cross section of the first portion and a second end having a cross section substantially identical to a cross section of the second portion.

28. The spinal stabilization system according to claim 27, wherein the first end is adjacent the first portion and the second end is adjacent the second portion.

29. The spinal stabilization system according to claim 25, wherein the connecting rod is monolithically formed.

30. A connecting rod for use in a spinal stabilization surgery, the connecting rod comprising:
an elongate rounded portion;
an elongate head portion having a non-circular cross-section; and
a neck portion connecting the elongate rounded portion with the elongate head portion, the neck portion having concave sides, wherein the neck portion has smaller dimensions than dimensions of the elongate rounded portion and the elongate head portion, wherein a cross-section of the connecting rod is asymmetric about an axis of the connecting rod, wherein the connecting rod is monolithically formed.

31. The spinal stabilization system according to claim 30, wherein the elongate head portion of the connecting rod has a substantially rectangular cross-section.

32. The spinal stabilization system according to claim 30, wherein the axis of the connecting rod extends through the neck portion.

* * * * *